(12) United States Patent
Yu et al.

(10) Patent No.: US 8,557,786 B2
(45) Date of Patent: Oct. 15, 2013

(54) MICRO RNA (MIRNA) AND NEUROFIBROMATOSIS TYPE 1: A ROLE IN DIAGNOSIS AND THERAPY

(75) Inventors: Xijie Yu, Orono, ME (US); Janet M. Hock, Bangor, ME (US)

(73) Assignee: Maine Institute of Human Genetics and Health, Brewer, ME (US)

( * ) Notice: Subject to any disclaimer, the term of this patent is extended or adjusted under 35 U.S.C. 154(b) by 205 days.

(21) Appl. No.: 13/059,862

(22) PCT Filed: Aug. 19, 2009

(86) PCT No.: PCT/US2009/054336
§ 371 (c)(1),
(2), (4) Date: May 16, 2011

(87) PCT Pub. No.: WO2010/022166
PCT Pub. Date: Feb. 25, 2010

(65) Prior Publication Data
US 2011/0224286 A1 Sep. 15, 2011

Related U.S. Application Data

(60) Provisional application No. 61/090,155, filed on Aug. 19, 2008.

(51) Int. Cl.
*A61K 48/00* (2006.01)
(52) U.S. Cl.
USPC ...................................................... 514/44 R
(58) Field of Classification Search
USPC ...................................................... 514/44 R
See application file for complete search history.

(56) References Cited

U.S. PATENT DOCUMENTS

2005/0261218 A1 11/2005 Esau et al.

FOREIGN PATENT DOCUMENTS

WO  07/148235 A2  12/2007
WO  WO 2008153692 A2 * 12/2008

OTHER PUBLICATIONS

Yang et al. (Cell (2004) v. 117, pp. 927-939).*

Garzon, Ramiro et al., "Distinctive microRNA signature of acute myeloid leukemia bearing cytoplasmic mutated nucleophosmin," PNAS, vol. 105(10):3945-3950 (2008).
Ferner, Rosalie E. et al., "International Consensus Statement on Malignant Peripheral Nerve Sheath Tumors in Neurofibromatosis 1," Cancer Research, vol. 62:1573-1577 (2002).
Garzon, Ramiro et al., "MicroRNA fingerprints during human megakaryocytopoiesis," PNAS, vol. 103(13):5078-5083 (2006).
Illmer, Thomas et al., "MiRNA Expression Signatures in Acute Myeloid Leukemia Are Predictors for Patient Outcome," Blood, Ash Annual Meeting Abstracts, vol. 108, Abstract No. 152 (2006).
Johnson, Steven M. et al., "RAS Is Regulated by the let-7 MicroRNA Family," Cell, vol. 120:635-647 (2005).
Lechman, Eric R. et al., "MicroRNA Expression Profiling in Sorted AML Subpopulations: a Possible Role for MiR-155/BIC in Stem Cell Maintenance and Leukemogenesis," Blood, ASH Annual Meeting Abstracts, vol. 106, Abstract No. 466 (2005).
Levy, Pascale et al., "Microarray-Based Identification of Tenascin C and TEnascin XB, Genes Possibly Involved in Tumorigenesis Associated with Neurofibromatosis Type 1," Clin. Cancer Res., vol. 13(2):398-407 (2007).
Ma, Li et al., "Tumour invasion and metastasis initiated by microRNA-10b in breast cancer," Nature, vol. 449 (7163):682-688 (2007).
Yang, Feng-Chun et al., "Hyperactivation of p21ras and PI3K cooperate to alter murine and human neurofibromatosis type 1-haploinsufficient osteoclast functions," The Journal of Clinical Investigation, vol. 116(11):2880-2891 (2006).
International Preliminary Report on Patentability for Application No. PCT/US09/54336, dated Nov. 1, 2010.
International Search Report for Application No. PCT/US09/54336, dated Apr. 2, 2010.
European Office Action for Application No. 09808780.2, dated Jul. 5, 2011.

* cited by examiner

*Primary Examiner* — Jon E Angell
(74) *Attorney, Agent, or Firm* — Wayne A. Keown; Furman Gregory Deptula

(57) ABSTRACT

The present invention shows that levels of certain micro RNAs (MiRNAs) are altered in NF1 cell lines and NF1 tumor cell lines as compared to non-NF1 controls. Methods are provided, e.g., to diagnose NF1 and NF1 tumors. Methods are also provided to treat NF1, NF1 related cancer, and cognitive deficits resulting from NF1.

10 Claims, 12 Drawing Sheets

Position 914-920 of NF 1 3' UTR    5'  ...CUAACUAAUUCUGAG---CAGGGUAA...    SEQ. ID NO.: 32
                                              |||||   |||||||
hsa-miR-10b                         3'      UGUUUAAGCCAAGAUGUCCCAU          SEQ. ID NO.: 17

Position 914-920 of NF 1 3' UTR    5'  ...CUAACUAAUUCUGAG---CAGGGUAA...    SEQ. ID NO.: 32
                                              |||||   |||||||
hsa-miR-10a                         3'      GUGUUUAAGCCAAGAUGUCCCAU         SEQ. ID NO.: 11

Position 1435-1441 of NF 1 3' UTR  5'  ...UUAAUCCCUUACUCCCAGGUUC           SEQ. ID NO.: 34
                                              ||  ||   |||||||
hsa-miR-490                         3'      GUCGUACCUCAGGA-GGUCCAAC         SEQ. ID NO.: 35

Position 650-656 of NF 1 3' UTR    5'  ...UAACACUUGAGUAUU----AGCAAUAA     SEQ. ID NO.: 36
                                              |||||    |||||||
hsa-miR-137                         3'      GAUGCGCAUAAGAAUUCGUUAU          SEQ. ID NO.: 37 let-7a does not have a target site in the NF1 3'UTR

Fig. 3

SEQUENCE LISTING

<160> NUMBER OF SEQ ID NOS: 44

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cacaaattcg gttctacagg gta                                            23

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ugagguagua gguuguauag uu                                             22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgaggtagta ggttgtatag tt                                             22

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 4
acauuuuucg uuauugcucu uga                                             23

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uuuuucauua uugcuccuga cc                                              22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acccacctgg agatccatgg                                                 20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctacgcgtat tcttaagcaa taa                                             23

<210> SEQ ID NO 8
<211> LENGTH: 22
<212> TYPE: RNA
<213> ORGANISM: Homo sapiens

<400> SEQUENCE: 8
ugagguagua gguuguauag uu                                              22

<210> SEQ ID NO 9
<211> LENGTH: 22
<212> TYPE: DNA
<213> ORGANISM: Homo sapiens

<400> SEQUENCE: 9
tgaggtagta ggttgtatag tt                                              22

<210> SEQ ID NO 10
<211> LENGTH: 80
<212> TYPE: RNA
<213> ORGANISM: Homo sapiens

<400> SEQUENCE: 10
ugggaugagg uaguagguug uauaguuuua gggucacacc caccacuggg agauaacuau     60
acaaucuacu gucuuuccua                                                 80

<210> SEQ ID NO 11
<211> LENGTH: 23

-continued

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uacccuguag aaccgaauuu gug                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atgggacatc ttggcttaaa cac                                              23

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ccauggaucu ccaggugggu                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtacctaga ggtccaccca                                                  20

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uuauugcuua agaauacgcg uag                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aataacgaat tcttatgcgc atc                                              23

<210> SEQ ID NO 17
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 17
uacccuguag aaccgaauuu gug                                            23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atgggacatc ttggcttaaa cac                                            23

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uguaaacauc cuacacucag cu                                             22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
acatttgtag gatgtgagtc ga                                             22

<210> SEQ ID NO 21
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cuguuaaugc uaaucgugau agggguuuuu gccuccaacu gacuccuaca uauuagcauu    60
aacag                                                                65

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uuaaugcuaa ucgugauagg ggu                                            23

<210> SEQ ID NO 23
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 23
cuccuacaua uuagcauuaa ca                                              22

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
aauuacgauu agcacuaucc cca                                             23

<210> SEQ ID NO 25
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uguuuugagc ggggggucaag agcaauaacg aaaaauguuu gucauaaacc guuuuucauu     60 auugcccug accuccucuc auuugcuaua uuca                                  94

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ucaagagcaa uaacgaaaaa ugu                                             23

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uuuuucauua uugcuccuga cc                                              22

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aguucucguu auugcuuuuu aca                                             23

<210> SEQ ID NO 29
<211> LENGTH: 83
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
cggggugagg uaguagguug ugugguuuca gggcagugau guugcccuc ggaagauaac    60 uauacaaccu acugccuucc cug                                           83

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugagguagua gguugugugg uu                                            22

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
cuauacaacc uacugccuuc cc                                            22

<210> SEQ ID NO 32
<211> LENGTH: 23
<212> TYPE: RNA
<213> ORGANISM: Homo sapiens

<400> SEQUENCE: 32
cuaacuaauu cugagcaggg uaa                                           23

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uacccuguag aaccgaauuu gu                                            22

<210> SEQ ID NO 34
<211> LENGTH: 23
<212> TYPE: RNA
<213> ORGANISM: Homo sapiens

<400> SEQUENCE: 34
uuaaucccuc uacucccagg uuc                                           23

<210> SEQ ID NO 35
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
```

-continued caaccuggag gacuccaugc ug                                                        22

<210> SEQ ID NO 36
<211> LENGTH: 23
<212> TYPE: RNA
<213> ORGANISM: Homo sapiens

<400> SEQUENCE: 36
uaacacuuga guauuagcaa uaa                                                       23

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uauugcuuaa gaauacgcgu ag                                                        22

<210> SEQ ID NO 38
<211> LENGTH: 31
<212> TYPE: DNA
<213> ORGANISM: Homo sapiens

<400> SEQUENCE: 38
attctgagca gggtaatcag tgaacaaagt g                                              31

<210> SEQ ID NO 39
<211> LENGTH: 31
<212> TYPE: DNA
<213> ORGANISM: Macaca mulatta

<400> SEQUENCE: 39
attctgagca gggtaatcag tgaacaaaga g                                              31

<210> SEQ ID NO 40
<211> LENGTH: 31
<212> TYPE: DNA
<213> ORGANISM: Mus sp.

<400> SEQUENCE: 40
attctaagca gggtaatttg cagacagagt g                                              31

<210> SEQ ID NO 41
<211> LENGTH: 31
<212> TYPE: DNA
<213> ORGANISM: Unknown
<220> FEATURE:
<223> OTHER INFORMATION: Description of Unknown: Unknown dog sequence

<400> SEQUENCE: 41
atcctgagca gggtaatcag tgaacaaagt g                                              31

<210> SEQ ID NO 42
<211> LENGTH: 31
<212> TYPE: DNA
<213> ORGANISM: Unknown
<220> FEATURE:
<223> OTHER INFORMATION: Description of Unknown: Unknown horse sequence

<400> SEQUENCE: 42
attctgagca gggtaatcag tgaacaaagt g                                              31

```
<210> SEQ ID NO 43
<211> LENGTH: 28
<212> TYPE: DNA
<213> ORGANISM: Unknown
<220> FEATURE:
<223> OTHER INFORMATION: Description of Unknown: Unknown opossum
      sequence

<400> SEQUENCE: 43
acttcaggca gggtcaccgg ggaaccca                                           28

<210> SEQ ID NO 44
<211> LENGTH: 31
<212> TYPE: DNA
<213> ORGANISM: Ornithorhynchus anatinus

<400> SEQUENCE: 44
attccaggca ggatagcctg tgaagttgga g                                      31
```

MICRO RNA (MIRNA) AND NEUROFIBROMATOSIS TYPE 1: A ROLE IN DIAGNOSIS AND THERAPY

RELATED APPLICATIONS

This application is a 35 U.S.C. §371 national stage filing of PCT Application No. PCT/US2009/054336 filed on Aug. 19, 2009, which claims priority to, and the benefit of, U.S. Patent Application No. 61/090,155 filed Aug. 19, 2008. The contents of the aforementioned applications are hereby incorporated by reference.

BACKGROUND OF THE INVENTION

Neurofibromatosis Type 1 (NF1; OMIM #162200) is the most common of autosomal dominant genetic disorders, affecting 1 in 3500 individuals worldwide (Riccardi et al. Am J Pathol 1994; 145:994-1000; Gutmann et al. JAMA 1997; 278:51-7). Currently more than 100,000 Americans suffer from NF1. NF1 is a tumor predisposition syndrome. The most common tumor pathologies in afflicted individuals are neurofibromas (100% incidence), malignant peripheral nerve sheath tumors (MPNST, 15% incidence), and optic gliomas (20% incidence). The NF1 patients may also have other issues, including cognitive deficits in children. In addition to neurofibromas which may occur in the nervous tissue, skin, bones, and muscles, the disease is also associated with hyperpigmented spots.

Multiple neurofibromas are the hallmark of NF1. One subtype of neurofibroma, the plexiform neurofibroma, occurs in about 30% of NF1 individuals. NF1 individuals with plexiform neurofibromas have up to 10% lifetime risk of developing malignant peripheral nerve sheath tumors (Evans et al. J Med Genet 2002; 39:311-4), the most common malignant tumors associated with NF1. Surgery is the only treatment for plexiform neurofibromas and MPNST; however complete surgical resection is often not possible. The prognosis for patients with MPNST is poor, with an overall 5-year survival rate of just 34% (Ducatman et al. Cancer 1986; 57:2006-21). Despite the urgent need, targeted therapies for MPNST to improve survival are not obvious.

Loss-of-function mutations in the NF1 tumor suppressor gene (often referred to herein as neurofibromin, the NF1 gene, or simply NF1) underlie these disease phenotypes. The NF1 tumor suppressor gene is often referred to herein interchangeably as the neurofibromin gene, the NF1 gene, or simply NF1, as will be easily understood by the skilled artisan. The skilled artisan will also understand that NF1 may refer to the disease state, i.e., the state of having Neurofibromatosis Type 1. The NF1-encoded protein, neurofibromin, has been shown to function as a Ras-GTPase activating protein (GAP). Neurofibromin converts Ras from its active GTP to its inactive GDP isoforms. Loss of function at NF1 dysregulates Ras oncogenic signaling pathway thus promotes abnormal cellular proliferation and tumorigenesis (Bollag G., and McCormick F. Nature 1992; 356:663-4). Many NF1-deficient tumors contain elevated levels of RAS-GTP and/or show upregulation of the RAS-dependent signaling pathway, supporting the notion that deregulated RAS signaling may contribute to tumor development (DeClue et al. Cell 1992; 69:265-73); Basu et al. Nature 1992. 356:713-5; Bollag G., et al. Nat Genet 1996. 12:144-8; Feldkamp et al. Surg Neurol 1999. 51:211-8; Ingram D A., et al. J Exp Med 2001.194:57-69). It is generally accepted that Schwann cells are the primary transformed cells in neurofibromas, and that loss of heterozygosity (LOH) of the NF1 locus in Schwann cells initiates tumorigenesis and development of neurofibromas. LOH of the NF1 locus has been found only in Schwann cells, but not in other cells in NF1 neurofibromas and MPNST (Kluwe L., et al. Genes Chromosomes Cancer 1999. 24:283-5; Rutkowski J L., et al. Hum Mol Genet 2000. 9:1059-66; Legius E., et al. Nat Genet 1993. 3:122-6). Mice with Schwann cell lineage specific ablation of the Nf1 gene develop neurofibromas (Zhu Y, et al. Science 2002. 296:920-2; Zhang L., et al. Proc Natl Acad Sci USA 2006. 103:9136-41; Wu J., et al. Cancer Cell 2008. 13:105-16). While the cells involved in NF1 neurofibroma tumorigenesis have been identified, little is known about the contributing gene networks, signaling pathways, and their upstream regulatory networks.

The fact that loss-of-function mutations in NF1 occur in both neurofibromas and MPNST suggests that NF1 mutations alone are not sufficient for neurofibromas to progress to MPNST. Recent research shows that certain neurofibroma subtypes accumulate additional changes, such as those affecting the $p19^{ARF}$-MDM2-TP53 and p16INK4A-Rb signaling cascades, resulting in their transformation into MPNST (Carroll, and Ratner. Glia 2008.56:1590-605). Deletions or other types of mutations in the p53 locus have been found in 29% to 75% of NF1 MPNST (Menon, et al. Proc Natl Acad Sci USA 1990. 87:5435-9); Legius, et al. Genes Chromosomes Cancer 1994. 10:250-5; Rasmussen, et al. Genes Chromosomes Cancer 2000. 28:425-31). Consistent with a role of p53 in the progression of MPNST, mice that harbor both Nf1 and Tp53 mutations develop MPNST (Cichowski, et al. Science 1999. 286:2172-6).

A few other gene changes, e.g. EGFR, TWIST1 and SOX10, have been implicated (Tabone-Eglinger, et al. Sarcoma 2008; 2008:849156; Miller, et al. Cancer Res 2006. 66:2584-91). However, there is less information on the regulatory networks related to NF1 MPNST transformation.

MicroRNAs (miRNAs) are potential upstream regulators of NF1 tumorigenesis and progression. miRNAs are a class of small non-coding RNAs of about 19-25 nucleotides that function as negative post-transcriptional gene regulators; and can regulate the entire set of genes (Lim, et al. Nature 2005. 433:769-73). miRNAs hybridize to the 3' untranslated region (UTR) of target mRNAs and repress translation or mediate mRNA cleavage. miRNAs provide important regulatory functions in a variety of biological processes, including development, cell proliferation, differentiation, and apoptosis. Studies show that miRNAs critically regulate tumorigenesis and progression by targeting oncogenes, tumor suppressor genes, or genes related to proliferation, angiogenesis, and apoptosis (Hwang, et al. Br J Cancer 2006. 94:776-80; Hwang, et al. Br J Cancer 2007. 96 Suppl:R40-4). Different tumor types and tumors at various stages of differentiation exhibit unique miRNA profiles (Rouhi, et al. Mamm Genome 2008. 19:517-25; Visone, et al. Am J Pathol 2009. 174:1131-8).

Presently, there are no curative treatments for NF1 and NF1-tumors. Accordingly improved methods of diagnosing those at risk for developing NF1 and for treatment of NF1 would be of great benefit.

SUMMARY OF THE INVENTION

The present invention advances the art by showing that levels of certain micro RNAs (MiRNAs) are altered in NF-1 cell lines and NF-1 tumor cell lines as compared to non-NF-1 controls.

In one aspect, the invention pertains to a method of diagnosing whether a subject is at risk for developing Neurofibromatosis Type 1 (NF1) or a sign or symptom thereof, comprising (i) measuring in a test sample from the subject the level of at least one miRNA gene product in the test sample, wherein an alteration in the level of the at least one miRNA gene product in the test sample relative to the level of corresponding miRNA gene product in a control sample is indicative of the subject being at risk for developing NF1, wherein the at least one miRNA gene product is selected from the group consisting of miR-10b, pre-miR-10b, miR-155, pre-miR-155, miR-335, pre-miR355, let-7a, pre-let7a, let-7b, and pre-let7b.

In one embodiment, the miR-10b gene product is present at a level significantly higher than that present in the control sample.

In one embodiment, the let-7a gene product is present at a level significantly lower than that present in the control sample.

In one embodiment, the miR-10b gene product is measured and the method further comprises measuring neurofibromin expression.

In one embodiment, the let-7a gene product is measured and the method further comprises measuring the level of activation of the Ras signaling pathway.

In another aspect, the invention pertains to a method of diagnosing whether a subject has, or is at risk for developing NF1 tumor, leukemia or NF1-related pathologies, comprising (i) measuring in a test sample from the subject the level of at least one miRNA gene product in the test sample, wherein an alteration in the level of miRNA gene product in the test sample relative to the level of corresponding miRNA gene product in a control sample is indicative of the subject either having, or being at risk for developing, NF1 tumor, leukemia or NF1-related pathologies, wherein the at least one miRNA gene product is selected from the group consisting of miR-10b, pre-miR-10b, miR-155, pre-miR-155, miR-335, pre-miR355, let-7a, pre-let7a, let-7b, pre-let7b, miR-137, pre-miR-137, miR-490, pre-miR-490.

In another aspect, the invention pertains to a method of increasing neurofibromin expression in a target cell comprising contacting the cell with an effective amount of a miR-10b inhibitor which downmodulates the level of miR-10b miRNA in a cell, such that neurofibromin expression in the target cell is increased.

In still another aspect, the invention pertains to a method of decreasing the activity of the Ras signaling pathway in a target cell comprising contacting the cell with an effective amount of a let-7a enhancer which upmodulates the level of Let-7a in a cell, such that the activity of the Ras signaling pathway in the target cell is decreased.

In yet another aspect, the invention pertains to a method of treating a subject having NF1 comprising, administering to the subject an effective amount of an agent which modulates the level of at least one miRNA gene product in a target cell, wherein the at least one agent is selected from the group consisting of a miR-10b inhibitor and a let-7a enhancer.

In one embodiment, the miR-10b inhibitor is an miR-10b antagomir comprising a nucleotide sequence having complementarity to miR-10b.

In one embodiment, the miR-10b antagomir comprises the nucleotide sequence 5'-CACAAATTCGGTTCTA-CAGGGTA-3'. [SEQ. ID NO.: 1]

In some embodiments the miR-10b inhibitor inhibits miR-10b indirectly by inhibiting TWIST1.

In some embodiments the antigomir or synthetic miRNA of the invention has a stabilizing modification. In some embodiments the stabilizing modification comprises a phosphorothioate backbone. In other embodiments the stabilizing modification comprises at least one nucleotide having a 2'-sugar modification.

In other embodiments the antigomir or synthetic miRNA of the invention has a cholesterol modification.

In one embodiment, the let-7a enhancer comprises a synthetic miRNA having at least one stabilizing modification.

In one embodiment, the synthetic miRNA comprises the nucleotide sequence 5'UGAGGUAGUAGGUU-GUAUAGUU 3' [SEQ. ID NO.: 2] or 5' TGAGGTAGTAG-GTTGTATAGTT 3'. [SEQ. ID NO.: 3]

In one embodiment, the at least one stabilizing modification comprises a phosphorothioate backbone.

In one embodiment, the at least one stabilizing modification comprises at least one nucleotide having a 2'-sugar modification.

In another aspect, the invention pertains to a method of treating a subject having or at risk for developing a NF1-tumor, leukemia or NF1-related pathologies comprising, administering to the subject an effective amount of an agent which modulates the level of at least one miRNA gene product in a target cell, wherein the at least one agent is selected from the group consisting of a miR-10b inhibitor, a miR-335 inhibitor, a miR-490 inhibitor, and a miR-137 inhibitor.

In one embodiment the agent is a miR-335 antigomir comprising a nucleotide sequence having complementarity to miR-335, pre-miR-335, mature miR-335 or miR-335*. In one embodiment the antigomir RNA comprises the nucleotide sequence 5'-ACAUUUUUCGUUAUUGCUCUUGA-3'. [SEQ. ID NO. 4] In another embodiment the antigomir RNA comprises the nucleotide sequence 5'-UUUUUCA-UUAUUGCUCCUGACC-3'. [SEQ. ID NO.: 5]

In one embodiment the agent is a miR-10b antigomir comprising a nucleotide sequence having complementarity to miR-10b, pre-miR-10b, mature miR-10b, or miR10b*. In one embodiment the antigomir RNA comprises the nucleotide sequence 5'-CACAAATTCGGTTCTACAGGGTA-3'. [SEQ. ID NO.: 1]

In one embodiment, the agent is a miR-490 antigomir comprising a nucleotide sequence having complementarity to miR-490.

In one embodiment, the antigomir RNA comprises the nucleotide sequence 5'ACCCACCTGGAGATCCATGG-3'. [SEQ. ID NO.: 6]

In one embodiment, the agent is a miR-137 antigomir comprising a nucleotide sequence having complementarity to miR-137

In one embodiment, the antigomir comprises the nucleotide sequence 5' ctacgcgtattcttaagcaataa 3'. [SEQ. ID NO.: 7]

In one embodiment, the method further comprises administering another anti-tumor therapeutic.

In one aspect, the invention pertains to a method of ameliorating cognitive defects in a juvenile subject with NF1, NF1-tumor, leukemia, or NF1-related pathologies comprising, administering to the subject an effective amount of an agent which decreases the level of the miR-10 gene miRNA gene product in a target cell.

In one embodiment, the agent is a miR-10 antigomir comprising a nucleotide sequence having complementarity to miR-10b.

In one embodiment, the antigomir comprises the nucleotide sequence 5' cacaaattcggttctacagggta 3'.

In one embodiment, a antigomir of the invention is 19 to 24 nucleotides in length.

In another embodiment, the antigomir has at least 95% percent complementarity to the miRNA over its full length, and wherein the 8 nucleotides at the 5' end of the antigomir are 100% complementary to the corresponding nucleotides of the miRNA.

In one embodiment, the antigomir comprises a cholesterol modification.

In one embodiment, the target cell is a neural crest cell.
In one embodiment, the target cell is a neural cell.
In one embodiment, the target cell is a Schwann cell.
In one embodiment, the agent is administered directly into the central nervous system.

In some preferred embodiments of the invention, a target cell is a nerve cell, a nerve sheath cell, a Schwann cell, an epithelial cell, an immune cell, or a bone cell.

In another aspect, the invention pertains to a method of identifying an agent that ameliorates at least one sign or symptom associated with NF1, comprising (i) contacting a cell with a test agent, (ii) measuring the effect of the test agent on the level of at least one miRNA gene product in the cell, wherein an alteration in the level of the at least one miRNA gene product in the cell relative to an appropriate control identifies the test agent as one which ameliorates at least one sign or symptom associated with NF1, wherein the at least one miRNA gene product is selected from the group consisting of miR-10b, pre-miR-10b, miR-355, pre-miR-355, let-7a, and pre-let7a.

In one embodiment, the level of a miR-10-b gene product is measured and the method further comprises measuring neurofibromin expression in the cell. In one embodiment, the level of a let-7a gene product is measured and the method further comprises measuring Ras signaling pathway in the cell.

In another aspect, the invention pertains to a method of identifying an agent that ameliorates at least one sign or symptom associated with a NF1-tumor, leukemia or NF1-related pathologies, comprising (i) contacting a cell with a test agent, (ii) measuring the effect of the test agent on the level of at least one miRNA gene product in the cell, wherein an alteration in the level of the at least one miRNA gene product in the cell relative to an appropriate control identifies the test agent as one which ameliorates at least one sign or symptom associated with a NF1-tumor, leukemia or NF1-related pathologies, wherein the at least one miRNA gene product is selected from the group consisting of miR-10b, pre-miR-10b, miR-137, pre-miR-137, miR-490, and pre-miR-490

In another aspect, the invention pertains to a method of identifying an agent that ameliorates at least one sign or symptom associated with NF1, NF1-tumor, leukemia or NF1-related pathologies, comprising (i) contacting a cell with a test agent, (ii) measuring the effect of the test agent on the level of TWIST1 in the cell, wherein an alteration in the level of TWIST1 in the cell relative to an appropriate control identifies the test agent as one which ameliorates at least one sign or symptom associated with NF1, NF1-tumor, leukemia or NF1-related pathologies. In some embodiments the level of TWIST1 is the gene expression level (e.g., the mRNA level). In another embodiment the level of TWIST1 is the protein level. In another embodiment the level of TWIST1 is the protein activity level.

In yet another aspect, the invention pertains to a method of identifying an agent that increases neurofibromin expression in a cell, comprising (i) contacting a cell with a test agent, (ii) measuring the effect of the test agent on the level of at least one miRNA gene product in the cell, wherein an alteration in the level of the at least one miRNA gene product in the cell relative to an appropriate control identifies the test agent as one which increases neurofibromin expression, wherein the at least one miRNA gene product is selected from the group consisting of miR-10b and pre-miR-10b.

In yet another aspect, the invention pertains to a method of diagnosing whether a subject has, or is at risk for developing a bone disorder, comprising (i) measuring in a test sample from the subject the level of at least one miRNA gene product in the test sample, wherein an alteration in the level of miRNA gene product in the test sample relative to the level of corresponding miRNA gene product in a control sample is indicative of the subject either having, or being at risk for developing, a bone disorder, wherein the at least one miRNA gene product is selected from the group consisting of miR-10b, pre-miR-10b, miR-155, pre-miR-155, miR-335, pre-miR355, let-7a, pre-let7a, let-7b, and pre-let7b.

In some preferred embodiments the bone disorder is scoliosis the miRNA gene product is miR-10b or pre-miR-10b. In other embodiments the miRNA gene product is miR-335. In particular embodiments the level of the miRNA gene product is elevated. In some preferred embodiments the bone disorder is NF1-related bone dysplasia, tibial dysplasia, skeletal growth defects, scoliosis, bone healing defects, osteopenia, osteoporosis, or tooth cementum overgrowth In yet another aspect, the invention pertains to a method of treating a subject having or at risk for developing a bone disorder comprising, administering to the subject an effective amount of an agent which modulates the level of at least one miRNA gene product in a target cell, wherein the at least one agent is selected from the group consisting of a miR-10b inhibitor and a miR-335 inhibitor. In particular embodiments, the miR-10b inhibitor is a nucleotide sequence having complementarity to miR-10b, mature miR-10b, miR-10b*, or pre-miR10b. In further embodiments, the miR-335 inhibitor is a nucleotide sequence having complementarity to miR-335, mature miR-335, miR-335*, or pre-miR 335. In particular embodiments the antigomir RNA comprises the nucleotide sequence 5'-ACAUUUUCGUUAUUGCUCUUGA-3' [SEQ. ID NO.: 4], the nucleotide sequence 5'-UUUUUCAUUAUUGCUCCUGACC-3' [SEQ. ID NO.: 5], or the nucleotide sequence 5'-CACAAATTCGGTTCTA-CAGGGTA-3'. [SEQ. ID NO.: 1]

In a further aspect, the invention provides a method of diagnosing whether a subject has, or is at risk for developing a NF1, an NF1-related tumor, or an NF1-related pathology, comprising (i) measuring in a test sample from the subject the level of at least one miRNA gene product in the test sample, wherein an alteration in the level of miRNA gene product in the test sample relative to the level of corresponding miRNA gene product in a control sample is indicative of the subject either having, or being at risk for developing, a neurofibromatosis-related tumor, wherein the at least one miRNA gene product is selected from the group consisting of miR-137, pre-miR-137, miR-490, and pre-miR-490.

In a related aspect, the invention provides a method of treating a subject having or at risk for developing an NF1, an NF1-related tumor, or an NF1-related pathology comprising, administering to the subject an effective amount of an agent which modulates the level of at least one miRNA gene product in a target cell, wherein the at least one agent is selected from the group consisting of a miR-490 inhibitor and a miR-137 inhibitor.

In some embodiments the agent is a miR-490 antagomir comprising a nucleotide sequence having complementarity to miR-490. In some embodiments the antigomir RNA comprises the nucleotide sequence 5'-ACCCACCTGGAGATC-CATGG-3'. [SEQ. ID NO.: 6]

In other embodiments the agent is an miR-137 antagomir comprising a nucleotide sequence having complementarity to miR-137 In some embodiments the antigomir comprises the nucleotide sequence 5'-CTACGCGTATTCTTAAG-CAATAA-3'. [SEQ. ID NO.: 7]

In further embodiments the method comprises administering another anti-tumor therapeutic in addition to the agent.

In another aspect the invention provides a method of identifying an agent that ameliorates at least one sign or symptom associated with NF1, an NF1-related tumor, or an NF1-related pathology, comprising (i) contacting a cell with a test agent, (ii) measuring the effect of the test agent on the level of at least one miRNA gene product in the cell, wherein an alteration in the level of the at least one miRNA gene product in the cell relative to an appropriate control indentifies the test agent as one which ameliorates at least one sign or symptom associated with a NF1, an NF1-related tumor, or an NF1 related pathology, wherein the at least one miRNA gene product is selected from the group consisting of miR-137, pre-miR-137, miR-490, and pre-miR-490.

One of skill in the art will appreciate that pre-miRNAs, mature miRNAs, pri-miRNAs, miRNA*s and fragments thereof may be preferred in some embodiments of the methods or compositions described herein. For example, antigomirs of the invention may be designed from or comprise an miRNA sequence, its mature form, a pri-miRNA, an miRNA*, or complements or fragments thereof.

BRIEF DESCRIPTION OF THE DRAWINGS

FIG. 3 depicts the target sites in the NF1 3'UTR for several miRNAs.

Figure 1A:
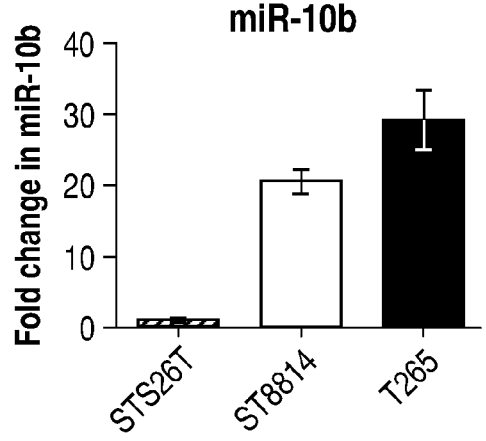
FIG. 1 depicts fold change in expression for several miR-NAs in tumor and normal cell lines. miR-10b, 137, 490 were found to be over-expressed in NF1 Schwann tumor cell lines (ST8814 and T265), compared to non-NF1 Schwann tumor cell lines (STS26T). The level of MiR-10b was found to be 20-30 fold higher in tumor cells while miR-137 was found to be 5 fold higher. The level of MiR-490 was found to be about 20-70 fold higher in tumor cells. The level of let-7a was reduced by half in NF1 Schwann tumor cell lines.
Figure 1B:
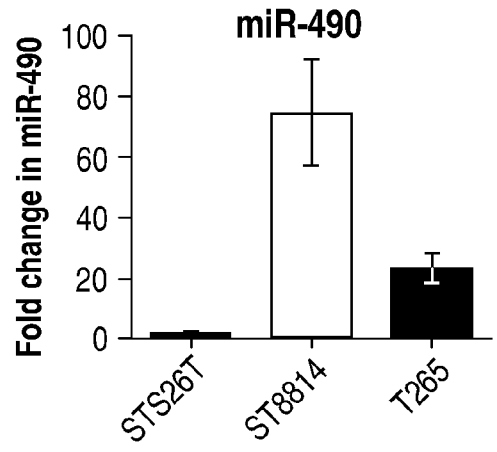
Figure 1C:
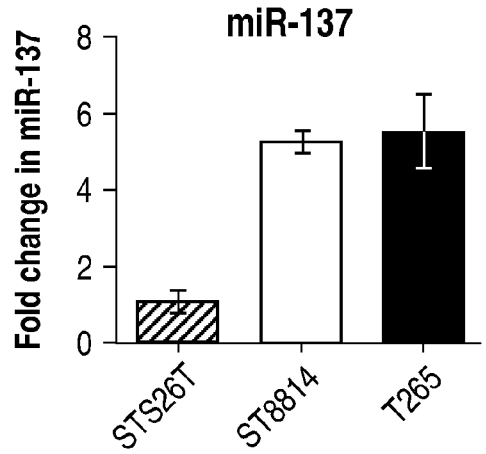
Figure 1D:
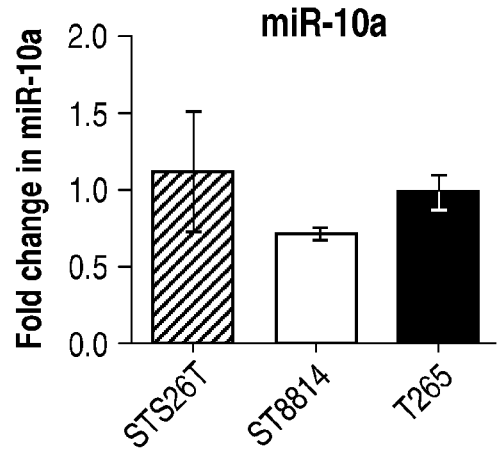
Figure 1E:
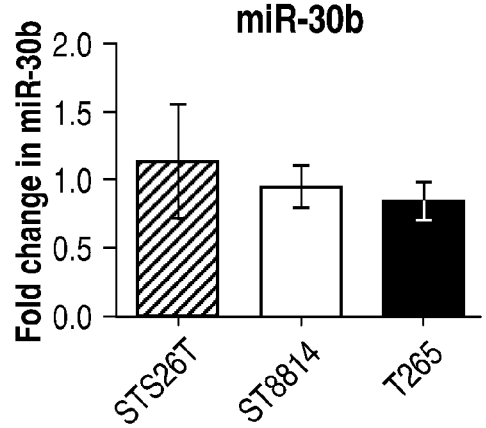
Figure 1F:
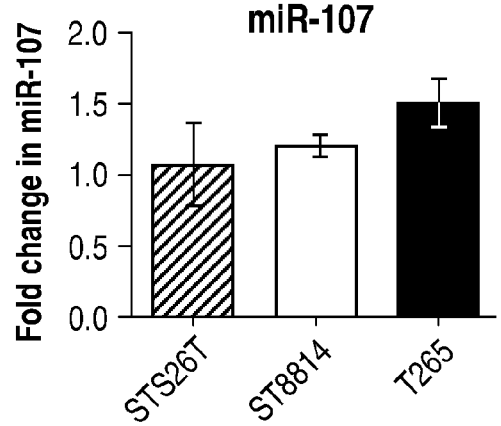
Figure 2A:
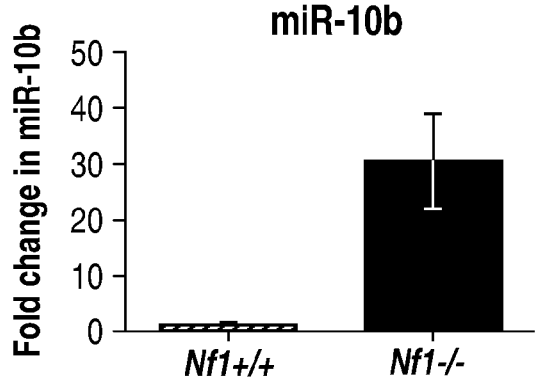
FIG. 2 depicts the expression of miRNAs in mouse embryonic stem (ES) cells: Nf1 wildtype (Nf1+/+) ES cells vs. Nf1 knockout (Nf1−/−) ES cells. Nf1−/− ES cells showed higher expression of miR-10b, lower expression of let-7a, and no change in miR-30b. Higher expression of miR-10a was also observed, and there was no change in miR-490 in Nf1−/− ES cells
Figure 2B:
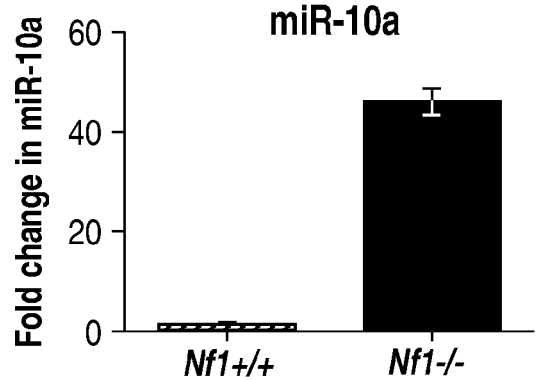
Figure 2C:
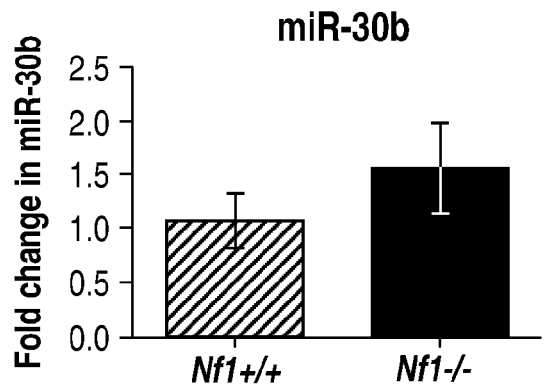
Figure 2D:
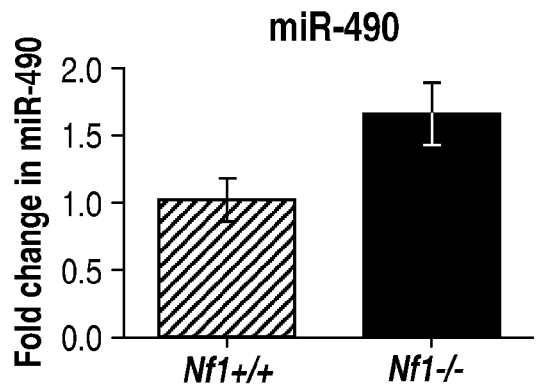
Figure 2E:
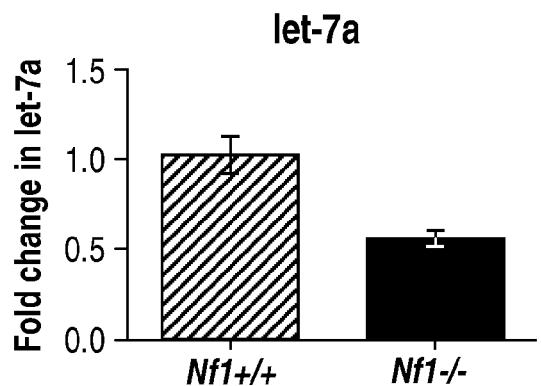

MTT assay). C: Inhibiting miR-155 or miR335, or enhancing let-7a expression had no effect on cell migration (n=3). D: Inhibiting miR-335 or enhancing let-7a expression significantly decreased cell invasion (n=3). vs. negative control: *P<0.05, P<0.01, *p<0.001.

DETAILED DESCRIPTION OF THE INVENTION

The present invention addresses the unmet need to provide diagnostics and therapeutics for NF1 and NF1-related diseases, e.g., NF1-tumors. The invention involves delivery to cells (in vivo or in vitro) of agents that modulate miRNAs, including but not limited to oligonucleotides, e.g., that are substantially antisense to at least a portion of an miRNA, oligonucleotides that comprise an miRNA sequence (e.g., oligonucleotides having stem-loop structures or miRNA duplexes) and/or expression vectors that encode oligonucleotides sequences.

I. Definitions

Before further description of the invention, certain terms are defined below:

As used herein the terms "miR," "mir," and "miRNA" are used to refer to microRNA, a class of small RNA molecules that are capable of modulating RNA levels (see, Zeng and Cullen, RNA, 9(1):112-123, 2003; Kidner and Martienssen Trends Genet, 19(1):13-6, 2003; Dennis C, Nature, 420(6917):732, 2002; Couzin J, Science 298(5602):2296-7, 2002, each of which is incorporated by reference herein).

MiRNAs are a new class of small non-coding RNAs that generally function as negative post-transcriptional gene regulators. MiRNAs typically hybridize to the 3' untranslated region (UTR) of target RNAs, often mRNAs, and mediate translational repression or RNA cleavage/destruction. Recent studies have shown that miRNAs provide important regulatory functions in a variety of biological processes including cell proliferation, differentiation, development, and apoptosis; it has also been linked to many cancers and may play a fundamental role in progression to cancer.

Without being bound to theory, a gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop, and the stem may comprise mismatched bases.

The hairpin structure of the pri-miRNA may be recognized by Drosha, which is an RNase III endonuclease. Processing by Drosha may yield a pre-miRNA stem loop having a 5' phosphate and about a 2 nucleotide 3' overhang. The details of pri-miRNA processing are well known in the art, an may be found, e.g., in U.S. Pat. Appl. 20070050146, which is incorporated herein by reference. It is thought that the pre-miRNA is recognized by Dicer, which is also an RNase III endonuclease, and further processed. The resulting siRNA-like duplex, which may comprise mismatches, comprises the mature miRNA and a similar-sized fragment known as the miRNA* (miRNA star). The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as single-stranded RNAs into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA (Yekta et al 2004, Science 304-594).

As used herein, the term "miRNA gene product" is any product of transcription from an miRNA gene including, the primary transcript, the pri-miRNA, the pre-miRNA, miRNA*, or the mature miRNA.

Preferred nucleic acids of the invention include let-7a, pre-let7a, miR-10b, pre-miR-10b, miR490, pre-miR-490, miR-137, pre-miR-137, miR-30b, miR-10a, pre-miR-30b, pre-miR10a, miR-155, pre-miR155, miR-355, pre-miR355, or nucleic acid molecules having complementarity thereto.

Human let-7a has the following sequence UGAGGUAGUAGGUUGUAUAGUU [SEQ. ID NO. 8] (DNA: TGAGGTAGTAGGTTGTATAGTT) [SEQ. ID NO. 9] and is contained in the pre-miRNA (UGGGAUGAGGUAGUAGG-UUGUAUAGUUUUAGGGUCACACCCACCACUGG GAGAUAACUAUACAAUCACUGUCUUUCCUA).
[SEQ. ID NO.:10] Other preferred miRNA sequences are as follows: hsa-miR-10b (UACCCUGUAGAACCGAAUUU-GUG [SEQ. ID NO.: 11], complement sequence: CACAAATTCGGTTCTACAGGGTA) [SEQ. ID NO.: 1], hsa-miR-490 (CCAUGGAUCUCCAGGUGGGU [SEQ. ID NO.: 13], complement sequence: ACCCACCTGGAGATC-CATGG) [SEQ. ID NO. 6], hsa-miR-137 (UUAUUGCU-UAAGAAUACGCGUAG [SEQ. ID NO. 15], complement sequence: CTACGCGTATTCTTAAGCAATAA) [SEQ. ID NO.:7], hsa-miR-10b (UACCCUGUAGAACCGAAUUU-GUG [SEQ. ID NO.: 17], complement sequence: CACAAATTCGGTTCTACAGGGTA) [SEQ. ID NO.: 1], and miRNA-30b (UGUAAACAUCCUACACUCAGCU [SEQ. ID. NO.: 19], complement sequence: AGCTGAGTG-TAGGATGTTTACA).

Further preferred sequences of the invention are as follows (sequences below are obtained from miRbase at microrna-.sanger.ac.uk): miR-155 (hsa-mir-155 MI0000681: CUG-UUAAUGCUAAUCGUGAUAGGGGU-
UUUUGCCUCCAACUGACUCCUACA
UAUUAGCAUUAACAG [SEQ. ID NO.: 21]; hsa-miR-155, mature sequence MIMAT0000646: UUAAUGC-UAAUCGUGAUAGGGGU [SEQ. ID NO.: 22]; hsa-miR-155* MIMAT0004658: CUCCUACAUAUUAGCA-UUAACA; [SEQ. ID NO.: 23]; miR-155 mature sequence complement: ACCCCUAUCACGAUUAGCAUUAA); miR-335 (hsa-mir-335 MI0000816: UGUUUUGAGCGGGGGU-CAAGAGCAAUAACGAAAAAUGUUUGUCAUAAAC CGUUUUCAUUAUUGCUCCUGACCUCCU-
CUCAUUUGCUAUAUUCA [SEQ. ID NO.: 25]; hsa-miR-335 mature sequence, MIMAT0000765: UCAAGAG-CAAUAACGAAAAAUGU [SEQ. ID NO.: 26]; hsa-miR-335* MIMAT0004703: UUUUUCAUUAUUGCUCCUGACC [SEQ. ID NO.: 27]; miR-335 mature sequence complement: ACAUUUUUCG- UUAUUGCUCUUGA) [SEQ. ID NO.: 4]; let-7b (hsa-let-7b MI0000063: CGGGGUGAGGUAGUAGGUUGUGUGGU-UUCAGGGCAGUGAUGUUGCCCCU CGGAA-GAUAACUAUACAACCUACUGCCUUCCCUG [SEQ. ID NO.: 29]; hsa-let-7b mature sequence, MIMAT0000063: UGAGGUAGUAGGUUGUGUGGUU [SEQ. ID NO.: 30]; and hsa-let-7b* MIMAT0004482: CUAUACAAC-CUACUGCCUUCCC [SEQ. ID NO.: 31]). In some embodiments, it is preferred to measure the expression level or activity of the miRNA sequence. In other embodiments it is preferred to measure the expression level or activity of the mature miRNA sequence. In yet other embodiments it is preferred to measure the expression level or activity of the miRNA* sequence.

The methods for the detection of miRNA sequences described herein (e.g., diagnostic and predictive methods) may be employed to detect the primary miRNA transcript, the mature miRNA, or complements thereof. When, according to the methods of treatment described herein (e.g., methods of treating a subject having or at risk for developing a NF1 tumor, leukemia or NF1-related pathologies, or methods of ameliorating cognitive defects in a juvenile subject having NF1), it is desirable to upmodulate or downmodulate the level of a miRNA of the invention, the complement of the primary miRNA transcript or the complement of the mature miRNA may be used (e.g., as an antigomir or an antisense regulator). In similar embodiments, the complement of the pri-miRNA may be used. In other embodiments the miRNA* sequence (or its complement) may be employed. In particular embodiments, it may be desirable to prepare an inhibitory (e.g., an antigomir or antisense sequence) to an miRNA* to up or downmodulate its level in a target cell. One of skill in the art will appreciate that a complementary sequence need not be an exact complement, and that it is within the scope of the present invention to employ miRNA fragments, fragments of complement sequences, or sequences which are similar to the miRNA or its complement. As one example, the level of miR-10b may be downmodulated using a sequence which is complementary to miR-10b, a fragment of the miR-10b complement, or, e.g., a sequence which is 80%, 85%, 90%, 95%, or 99% identical to the complement of miR-10b. When an inhibitor, enhancer, or other agent "upmodulates" or "downmodulates" a nucleic acid (e.g., an miRNA, pre-miRNA, miRNA*, or pri-miRNA) it should be understood that the inhibitor, enhancer, or agent increases or decreases, respectively, the expression of the nucleic acid.

As used herein, when an expression level or activity is "significantly higher" the expression level or activity is measurably higher than a control sample or it is measurably higher than a sample from a subject not having NF1 (or NF1-tumor, or NF1-related pathologies) and would be understood by one of ordinary skill in the art to be biologically significant. In some embodiments "significantly higher" indicates that the higher expression level or activity is statistically significant, e.g., having a p-value on a t-test (or equivalent parametric or non-parametric statistical test) of less than 0.1, less than 0.07, less than 0.05, less than 0.01, less than 0.005, less than 0.001, less than 0.0005, or less than 0.0001. In other embodiments "significantly higher" indicates that the expression level or activity is higher by 1 or 2-fold. In other embodiments, the "significantly higher" indicates that the expression level or activity is higher by 3 to 5-fold, or 5-10-fold. In other embodiments, the "significantly higher" indicates that the expression level or activity is higher by 10-fold, 12-fold, 15-fold, 20-fold, 25-fold, 30-fold, 35-fold, or 40-fold or more.

As used herein, when an expression level or activity is "significantly lower" the expression level or activity is measurably lower than a control sample or it is measurably lower than a sample from a subject not having NF1 (or NF1-tumor, or NF1-related pathologies) and would be understood by one of ordinary skill in the art to be biologically significant. In some embodiments "significantly lower" indicates that the lower expression level or activity is statistically significant, e.g., having a p-value on a t-test (or equivalent parametric or non-parametric statistical test) of less than 0.1, less than 0.07, less than 0.05, less than 0.01, less than 0.005, less than 0.001, less than 0.0005, or less than 0.0001. In other embodiments "significantly lower" indicates that the expression level or activity is lower by 1 or 2-fold. In other embodiments, the "significantly lower" indicates that the expression level or activity is lower by 3 to 5-fold, or 5-10 fold. In other embodiments, the "significantly lower" indicates that the expression level or activity is lower by 10-fold, 12-fold, 15-fold, 20-fold, 25-fold, 30-fold, 35-fold, or 40-fold or more.

As used herein, "treatment" is a clinical intervention made in response to a disease, disorder or physiological condition manifested by a patient or to which a patient may be susceptible. The aim of treatment includes the alleviation or prevention of at least one sign and/or symptom, slowing or stopping the progression or worsening of a disease, disorder, or condition and/or the remission of the disease, disorder or condition. "Treatments" or "treating" refer to one or both of therapeutic treatment and prophylactic or preventative measures. Those in need of treatment include those already affected by a disease or disorder or undesired physiological condition as well as those in which the disease or disorder or undesired physiological condition is to be prevented.

A "symptom" or "sign" of a disease, as used in the present methods, is subjective or objective evidence of the disease. Subjective evidence or suggestion of disease may be a sensation by a patient or a change in a patient's appearance or bodily function. For example, a symptom of pain may be a subjective determination by the patient as to how much pain the patient is feeling. Objective evidence or suggestion of disease may include qualitative and/or quantitative test results, or the diagnosis of a doctor. For example, the presence of neurofibromas may be objective evidence of NF1.

In one embodiment, the methods of the invention can be used to slow or prevent the progression of patients with NF1 to MPNST.

As used herein "NF1-related tumor," "NF1-related cancer," and "NF1-tumor" is a tumor or cancer which occurs as a result of NF1. Examples of NF1-tumors and cancers include malignant brain tumors, leukemia juvenile leukemia, Schwannomas, nerve tumors, acoustic neuromas, nerve sheath tumors, and tumors of certain muscles (rhabdomyosarcoma), neurofibroma, adrenal gland tumors (pheochromocytoma), cancer of the kidney (e.g., Wilms' Tumor) or ureter, carcinoma of the renal pelvis, neoplasm of the central nervous system (CNS), spinal axis tumor, brain stem glioma, pituitary adenoma, malignant glioma, optic glioma, paraspinal neurofibromas, intraspinal tumors, plexiform neurofibromas, and others known to clinicians to be associated with the disease.

Traditionally the diagnostic criteria for NF1 include the presence of two or more of the following (see U.S. Pat. No. 5,391,575, incorporated herein by reference): (1) six or more cafe-au-lait (hyperpigmented) macules more than 15 mm in greatest diameter in postpubertal individuals, or 5 mm in prepubertal individuals; (2) two or more neurofibromas of any type, or one plexiform neurofibroma; (3) freckling in the axillary or inguinal regions; (4) optic glioma; (5) two or more Lisch nodules (iris hamartomas); (6) a distinctive bony lesion such as sphenoid dysplasia or thinning of long-bone cortex, with or without pseudoarthrosis; (7) a first degree relative with NF1 (Von Recklinghausen, F., "Uber die multiplen fibrome der Haut and ihre Beziehung zu den multiplen, "Neuromen.," Hirschwald, Berlin (1882)). Other signs/symptoms of NF1 may include short stature, skeletal abnormalities (e.g., scoliosis), macrocephaly, and often learning disabilities such as attention deficit hyperactivity disorder (ADHD), low IQ, behavioral difficulties, or other cognitive defects. "Cognitive defects," which often occur in children, may be the result of neurofibromas which affect the nervous tissue or brain, other brain tumors, Schwannomas, or be due to the effects of the loss of neurofibromin (the NF1 tumor suppressor gene) in the nervous tissue. In one embodiment, the therapeutic methods described herein may be used to ameliorate one or more of these symptoms.

To carry out the methods of the invention, e.g., diagnostic methods, miRNA may be harvested from a biological sample such as a tissue or a biological fluid. The tissue may be both localized and/or disseminated cell populations including, but not limited to brain, heart, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. Tissue and fluid samples may be obtained from cancerous, precancerous, non-cancerous, or benign tissues. For example, in some embodiments samples may be collected from a NF1-tumor or from a tissue near a NF1-tumor. Biological fluids include saliva, sperm, serum, plasma, blood, ocular lens fluid, cerebral spinal fluid, sweat, urine, milk, ascites fluid, mucous, synovial fluid, peritoneal fluid, and amniotic fluid, but are not so limited. Both invasive and non-invasive techniques can be used to obtain such samples and are well documented in the art. In some embodiments, the miRNA are harvested from one or few cells. A "test sample" as used herein, is a biological specimen suspected of containing the miRNA sequences, or variants thereof. The test sample can be derived from any biological source, such as a physiological fluid (e.g., see the list of biological fluids above), or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, preparing liquids from solid materials, preparing cells from a tissue sample, isolating nucleic acid from tissues or cells, diluting viscous fluids, filtering liquids, distilling liquids, concentrating liquids, inactivating interfering components, adding reagents, and the like. Test samples also can be pretreated to digest, restrict or render double stranded nucleic acid sequences single stranded. Moreover, test samples may be pretreated to accumulate, purify, amplify or otherwise concentrate sequences that may be contained therein. Amplification reactions that are well known in the art can be used to amplify target sequences.

As used herein "NF1-related pathologies" or "NF1-related diseases" include NF1, NF1-related diseases, and signs or symptoms associated with NF1. For example, without being limited to any one list, NF1-related pathologies include cognitive defects, bone disorders (e.g., as described herein), NF1-tumor(s), e.g., as described herein, leukemia, nerve tumors, nerve sheath tumors, peripheral nerve sheath tumors, MPNST, growth hormone deficiency, neurofibromas, paraspinal neurofibromas, intraspinal tumors, plexiform neurofibromas, bone overgrowth, bone erosion, bone distortion, bumps under the skin, disordered skin pigmentation, café au lait spots, freckling of the groin or the arm pit, lisch nodules, and freckling of the iris.

II. Nucleic Acid Molecules of the Invention

As used herein the term "oligonucleotide" or "polynucleotide" may mean at least two nucleotides covalently linked together. As will be appreciated by those in the art, the depiction of a single strand also defines the sequence of the complementary strand. Thus, disclosure of a single stranded nucleic acid molecule also constitutes disclosure of the complementary strand of a depicted single strand based on Watson-Crick base pairing.

As will also be appreciated by those in the art, many variants of a nucleic acid molecule may be used for the same purpose as a given nucleic acid molecule. Thus, a nucleic acid also may also encompass substantially identical nucleic acids and complements thereof, as well as modified versions of nucleic acid molecules, e.g., comprising chemical modifications or additional moieties that confer beneficial properties to the nucleic acid molecule. A nucleic acid molecule may also encompass a probe that hybridizes to another nucleic acid molecule under stringent hybridization conditions.

In some preferred embodiments a nucleic acid molecule of the invention has 5, 10, 15, 16, 17, 18, 19, 20, 21, 22, 23, 24, 25, 26, 27, 28, 29, 30, 31, 32, 33, 34, 35, 40, or 50 etc. bases or nucleotides Nucleic acid molecules of the invention may be single stranded or double stranded, or may contain portions of both double stranded and single stranded sequence (i.e., may be part double stranded and part single stranded). A nucleic acid molecule may be DNA (e.g., genomic or cDNA) RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods which are well known in the art.

In some embodiments, nucleic acid molecules, e.g., an miRNA, may be isolated, e.g., from vertebrate cells such as mammalian cells. Preferred nucleic acid molecules of the invention are isolated. An "isolated" molecule, as used herein, is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing. Because an isolated molecular species of the invention may be admixed with a pharmaceutically-acceptable carrier in a pharmaceutical preparation, the molecular species may comprise only a small percentage by weight of the preparation. The molecular species is nonetheless isolated in that it has been substantially separated from the substances with which it may be associated in living systems, e.g. adjacent genomic nucleic acid sequences.

A nucleic acid molecule will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference.

Nucleic acid molecules containing one or more non-naturally occurring or modified nucleotides are also included within one definition of nucleic acid molecules. The one or more modified nucleotide analog may be located for example at the 5'-end and/or the 3'-end of the nucleic acid molecule or within the nucleic acid molecule. Representative examples of nucleotide analogs may be selected from sugar- or backbone-modified ribonucleotides. It should be noted, however, that nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. In a preferred embodiment, a modified nucleic acid molecule of the invention comprises a 2'-O methyl modification.

Modifications of the ribose-phosphate backbone may be done for a variety of reasons, e.g., to increase the stability and half-life of such molecules in physiological environments or as probes on a biochip. Mixtures of naturally occurring nucleic acids and analogs may be made; alternatively, mixtures of different nucleic acid analogs, and mixtures of naturally occurring nucleic acids and analogs may be made. It will further be understood that combinations of modifications (e.g., modifications to backbone linkages and 2'O modifications) may be made to the same nucleic acid molecule. Stabilizing alterations may include the use of nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated.

In another embodiment, exemplary modifications to a nucleic acid molecule of the invention include the incorporation of an additional moiety. For example, in one embodiment, a nucleic acid molecule of the invention comprises a cholesterol moiety.

Preferred nucleic acid molecules of the invention include oligonucleotides, e.g., DNA or RNA molecules, such as pri-miRNA, pre-miRNA, miRNA, and anti-miRNA.

A. MicroRNA Enhancers miRNA enhancers are molecules, e.g., nucleic acid molecules, small molecules, which act to increase the level of a miRNA gene product in a cell.

In one embodiment, a miRNA enhancer may comprise a sequence of a miRNA, miRNA* or a variant thereof. In one embodiment, the miRNA molecule is a synthetic molecule. In one embodiment, the miRNA molecule comprises one or more stabilizing mutations. The miRNA sequence may comprise from 21-23, 21-25 13-33, 18-24, 18-26, or 21-23 nucleotides. In some embodiments the miRNA sequence may comprise 15, 16, 17, 18, 19, 20, 21, 22, 23, 24, 25, 26, 27, 28, 29, or 30 nucleotides. The sequence of the miRNA may be the first 13-33, or 21-25 nucleotides of the pre-miRNA. The sequence of the miRNA may be the last 13-33 or 21-25 nucleotides of the pre-miRNA.

The nucleic acid molecule of the invention may comprise a sequence of a pri-miRNA or a variant thereof. The pri-miRNA sequence may comprise from 30-300, 35-375, 45-250, 55-200, 70-150 or 80-100 nucleotides. The sequence of the pri-miRNA may comprise a pre-miRNA, miRNA and miRNA* as set forth below. The pri-miRNA may also comprise a miRNA or miRNA* and the complement thereof, and variants thereof.

The pri-miRNA may form a hairpin structure. The hairpin may comprise a first and second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than –25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4, 5, 6, 7, 8, 9, 10, 11, 12, 13, 14, 15, 16, 17, 18, 19, 20, 21, 22, 23, 24, or 25 nucleotides.

The nucleic acid of the invention may also comprise a sequence of a pre-miRNA or a variant thereof. The pre-miRNA sequence may comprise from 30-50, 40-100, 45-90, 60-80 or 60-70 nucleotides. The sequence of the pre-miRNA may comprise a miRNA and a miRNA* as set forth below. The pre-miRNA may also comprise a miRNA or miRNA* and the complement thereof, and variants thereof. The sequence of the pre-miRNA may also be that of a pri-miRNA excluding from 0-160, 0-150, 0-130, 0-120, 0-100, 0-80, 0-60, 0-50, 0-40, 0-30, 0-20, or 0-10 nucleotides from the 5' and 3' ends of the pri-miRNA.

B. MiRNA Inhibitors

In one embodiment, a nucleic acid molecule of the invention is an miRNA inhibitor. For example, in one embodiment, such an inhibitory nucleic acid molecule is an antigomir. As used herein, the term antigomir is an anti-miRNA molecule that is capable of blocking the activity of a miRNA or miRNA*. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, or 30 nucleotides. In one embodiment, the sequence of the anti-miRNA may comprise (a) at least 5 nucleotides that are substantially identical to the 5' of a miRNA and at least 5-12 nucleotide that are substantially complimentary to the flanking regions of the target site from the 5' end of said miRNA, or (b) at least 5-12 nucleotides that are substantially identical to the 3' of a miRNA and at least 5 nucleotide that are substantially complimentary to the flanking region of the target site from the 3' end of said miRNA.

The sequence of an anti-miRNA of the invention may comprise the compliment of a sequence of a miRNA such that, e.g., the anti-miRNA binds to the miRNA to block its activity.

C. Complementarity of Nucleic Acid Molecules

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 Genes Dev 2004-504). However, other parts of the microRNA may also participate in mRNA binding. Moreover, sufficient base pairing at the 3' can compensate for insufficient pairing at the 5' (Brennecke et al., 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et al. 2005 Cell 120-15). Similarly, nucleotides 1-7 or 2-8 were used to identify and validate targets by Krek et al. (2005, Nat Genet 37-495).

Nucleic acid inhibitors of an miRNA have complementarity to the miRNA molecule whose level is to be inhibited. In one embodiment, the inhibitor and the miRNA are 100% complementary over their full length (i.e., are complementary at 100% of the nucleotides of the miRNA molecule). In another embodiment, the inhibitor and the miRNA molecule are 99%, 98%, 97%, 96%, 95%, 94%, 93%, or 90% complementary over their full length. In embodiments where the molecules are less than 100% complementary, preferably, the 2, 3, 4, 5, 6, 7, 8, 9, or 10 bases at the 5' end of the miRNA molecule are complementary to the nucleotides present in the inhibitor at the corresponding position; mismatching may occur at other positions and the desired level of complementarity achieved.

"MicroRNA seed sequence," "miRNA seed sequence," "seed region" and "seed portion" are used to refer to nucleotides 2-7 or 2-8 of the mature miRNA sequence. The miRNA seed sequence is typically located at the 5' end of the miRNA. In some embodiments, an miRNA "seed" region for comparison may be designated in the miRNA sequence, and the UTR of potential target gene sequences may be selected on the basis of complementarity or perfect complementarity with the seed region of the miRNA. In some cases, the seed region nucleates binding between an miRNA and its complement, for example, a sequence that is substantially antisense to the miRNA sequence. The "seed" region is also referred to herein as a first portion of the miRNA sequence. The seed region of the miRNA may be any suitable portion of the miRNA, for example, 3, 4, 5, 6, 7, 8, 9, or 10 consecutive nucleotides within the miRNA sequence. Preferably, the seed region of the miRNA is 6, 7, or 8 consecutive nucleotides within the miRNA sequence. For instance, the seed region of the miRNA sequence may advantageously be inclusively defined as nucleotides 1 through 7, 1 through 8, 2 through 7, or 2 through 8 from the 5' end of the oligonucleotide. Other examples include 1 through 9, 1 through 10, 2 through 7, 2 through 8, 2 through 9, 2 through 10, 3 through 10, 4 through 12, etc. from the 5' end of the oligonucleotide. The portion of the UTR complementary to the seed region may be referred to as a "seed match" region or a first sequence of the UTR. After determining a match between the seed region of the miRNA and the seed match region of the UTR of the potential target gene sequence, an "extended" portion may be defined within the miRNA, where the extended portion includes nucleotides within the miRNA that are at least partially complementary (i.e., including G:U pairing), if not perfectly complementary, to the UTR of the potential target gene sequence. The sequence within the UTR that the extended portion of the miRNA binds to may also be referred to as an extended sequence within the UTR. In some cases, the extended portion of the miRNA may be defined by proceeding in the 3' and/or 5' directions from the seed region of the miRNA as far as possible, until a mismatch is found. In other cases, the extended portion may be defined as a portion of this. In some instances, the extended portion may have 1, 2, 3, 4, or more nucleotides, in addition to the seed region. In other instances, however, the extended portion may be determined to be the same as the seed region Accordingly, some embodiments, the targets of the miRNAs of the invention have sequence regions which are complementary to the miRNAs, often the 5' region of the miRNA. In some embodiments the target sequence is 100% identical to the seed region of the miRNA

III. Uses of the Invention

A. Diagnosing and Predicting NF1-Related Pathologies

The present invention also relates to a method of diagnosis comprising detecting a differential expression level of a disease-associated miRNA in a biological sample. The sample may be derived from a patient. Diagnosis of a disease state in a patient allows for prognosis and/or selection of therapeutic strategy. A differential expression of a disease-associated miRNA compared to a control may be used to diagnose a patient suffering from the disease or at risk of suffering from the disease (e.g., NF1, NF1-tumor, or NF1-related pathologies). Expression levels of a disease-associated miRNA may also be used to monitor the treatment and disease state of a patient. Furthermore, expression levels of disease-associated miRNA may allow the screening of drug candidates for altering a particular expression profile or suppressing an expression profile associated with disease.

In situ hybridization of labeled probes to tissue arrays may be performed. When comparing the levels of disease-associated miRNA between an individual and an appropriate control or standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

In one aspect, the invention provides diagnostic biomarkers for NF1 and NF1-related tumors. In a related aspect, the invention provides prognostic biomarkers to predict NF1 and NF1-related tumor development, e.g., the progression to MPNST.

In one embodiment the invention provides methods to diagnose or predict whether a subject is at risk for developing NF1 (or NF1-related pathologies), comprising, e.g., (i) measuring in a test sample from the subject the level of at least one miRNA gene product in the test sample, wherein an alteration in the level of the at least one miRNA gene product in the test sample relative to the level of corresponding miRNA gene product in a control sample is indicative of the subject being at risk for developing NF1 (or NF1-related pathologies). In some embodiments the miRNA gene product is chosen from the group consisting of miR-10b, pre-miR-10b, let-7a, pre-let7a, miR10a, and pre-miR10a. In one embodiment, more than one gene product is measured. In one embodiment, the gene product can be measured by determining the level of expression of the gene. In another embodiment, the activity of the gene product may be measured.

In some embodiments, a subject having or at risk for developing NF1 (or NF1-related pathologies) will exhibit altered levels of certain miRNAs. In some embodiments a subject having or at risk for developing NF1 (or NF1-related pathologies) has increased levels of miR-10b, and/or miR-10a. Accordingly, measuring the level or activity of miR-10b, pre-miR-10b, Mir-10a and/or pre-miR-10a in a subject, and determining one or more are elevated, may indicate that the subject has or is at risk of developing NF1, NF1-related pathologies, or NF1-tumors.

In some embodiments a subject having or at risk for developing NF1 (or NF1-related pathologies) has decreased levels of let-7a and/or let7b. Accordingly, measuring the level or activity of let-7a and/or let7b in a subject, and determining that it is decreased, may indicate that the subject has or is at risk of developing NF1, NF1-related pathologies, or NF1-tumors.

In one embodiment, measuring the level or activity of one or more of: i) miR-10b, pre-miR-10b, Mir-10a and/or pre-miR-10a; ii) miR-155, pre-miR155; and/or iii) miR-355, pre-miR355 in a subject, and determining one or more are elevated, may indicate that the subject has or is at risk of developing NF1 or NF1-related pathologies (e.g., tumor, bone disorders, etc.). In one embodiment, the level of let-7a and/or let-7b can also be measured and, if it is decreased compared to an appropriate control may indicate that the subject has or is at risk of developing NF1, NF1-tumor, leukemia or NF1-related pathologies, In another embodiment the invention provides methods to diagnose or predict whether a subject has, or is at risk for developing a NF1-tumor, leukemia or NF1-related pathologies, comprising (i) measuring in a test sample from the subject the level of at least one miRNA gene product in the test sample, wherein an alteration in the level of miRNA gene product in the test sample relative to the level of corresponding miRNA gene product in a control sample is indicative of the subject either having, or being at risk for developing NF1-tumor, leukemia or NF1-related pathologies. In some embodiments the miRNA gene product is miR-155, pre-miR155, miR-355, pre-miR355, miR-137, pre-miR-137, miR-490, pre-miR-490, miR-10b, and/or pre-miR-10b.

In some embodiments, a subject having or at risk for developing a NF1-tumor, leukemia or NF1-related pathologies will exhibit altered levels of certain miRNAs. In some embodiments a subject having or at risk for developing a NF1-tumor, leukemia or NF1-related pathologies has increased levels of miR-10b, miR-490, and/or miR-137. Accordingly, measuring the level or activity of miR-155, pre-miR155, miR-355, pre-miR355, pre-miR-10b, MiR-490, pre-miR-490, miR-137, and/or pre-miR-137 in a subject, and determining one or more are elevated, may indicate that the subject has or is at risk of developing a NF1-tumor, leukemia or NF1-related pathologies. In some embodiments a subject having or at risk for developing a NF1-tumor, leukemia or NF1-related pathologies has decreased levels of let-7a and/or let-7b. Accordingly, measuring the level or activity of let-7a and/or let7b in a subject, and determining that it is decreased, may indicate that the subject has or is at risk of developing a NF 1-related tumor.

In some embodiments a subject having or at risk for developing a NF1-tumor, leukemia and/or NF1 other related pathologies will have an alteration (e.g., a mutation or polymorphism) in an NF1 gene, e.g., a mutation or single nucleotide polymorphism that prevents or augments the regulation of NF1. Such a mutation or polymorphism may be present anywhere in the gene sequence. In some embodiments the alteration is in the NF1 promoter, the 5'UTR, or 3'UTR. In some embodiments, the alteration enhances the regulation of NF1 by miR-335 or miR-155. In some embodiments, the alteration is in the 3'UTR and enhances regulation of NF1 by miR-10b. In some embodiments, the alteration reduces or eliminates the regulation of NF1 by let-7a or let-7b. It will be understood by the skilled artisan that an alteration may exist in genes other than NF1 and still affect NF1 gene regulation. For example, alterations may exist in miR-10b, TWIST1, let-7a, let-7b, miR-335, miR-155, or others. It is within the scope of the present invention to detect alterations in NF1 and other genes which may affect neurofibromatosis type 1, NF 1-related tumor development, or NF1 gene regulation. Standard methods known in the art may be employed to detect such alterations. For example, DNA sequencing or an SNP array may be employed.

As used herein, "an alteration in the level of miRNA gene product" is used to indicate that the level of miRNA in a subject or sample is increased or decreased by some amount as compared to another sample, e.g., a control sample. In some embodiments the miRNA is increased or decreased by an amount between 1-fold and 20-fold, or more than 20-fold. In some particular embodiments the miRNA is increased or decreased by 1-fold, 2-fold, 3-fold, 4-fold, 5-fold, 7-fold, 9-fold, 10-fold, 12-fold, 15-fold, 20-fold, 25-fold or more. In other embodiments the miRNA is increased or decreased by 5%, 10%, 20%, 30%, 40%, 50%, 60%, 70%, 80%, 90%, 100%, 150%, 200%, 300%, or more. Indeed, any measurable change in the level of miRNA may be used in order to diagnose or predict NF1 or NF1-related pathologies. In one embodiment, the change in the level of miRNA is significant, i.e. would be recognized by one of ordinary skill in the art as being indicative of a biologically significant change in levels. In another embodiment, the change in level of miRNA is statistically significant.

The "level" of a nucleic acid as described in the present methods is the amount of the nucleic acid or its activity as measured by standard laboratory methods. The term may indicate the amount of nucleic acid (e.g., concentration or total amount) detected in a sample, e.g., by northern blot or microarray analysis, or may indicate the level of activity of a nucleic acid, as measured by, e.g., its ability to inhibit a target RNA or the amount by which it reduces the amount or activity of the protein encoded by the target RNA.

As used herein, the term "target" as used in the context of an miRNA target refers to the RNA which contains a binding site for the miRNA. Thus, the term "target" often refers to the RNA which is to be inhibited by the miRNA. In some embodiments the term "target" may be used in reference to the gene which encodes the target RNA. Similarly, in some embodiments the term "target" may be used to refer to the protein which is affected by the miRNA (e.g., an miRNA may bind to and inhibit the translation of an mRNA and thus reduce the amount of the "target" protein encoded by the mRNA). "Target" may also be used to refer to the specific sequence of nucleic acids which hybridize with the miRNA, or may be used to refer to the complement of the miRNA.

The target sites in target mRNA may be in the 5' UTR, the 3' UTR or in the coding region. Interestingly, multiple miRNAs may regulate the same mRNA target by recognizing the same or multiple sites. The presence of multiple miRNA complementarity sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity.

It should be notes that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

In one set of embodiments, target gene sequences for an miRNA sequence can be determined by comparing the sequence of potential target gene sequences with the miRNA sequence for complementary matches (e.g., for Watson-Crick complementarity pairing and/or G:U pairing). For example, the UTR of potential target gene sequences can be compared with the miRNA sequence for complementary matches, and used to identify those gene sequences with higher degrees of complementarity as being target gene sequences. The determination may be performed manually, or with the aid of a machine such as a computer system. The potential target gene sequences to be searched may be from one, or several species (for example, for comparative studies, i.e., human and mouse, human and rat, mouse and rat, human and pufferfish (Fugu), human and dog, human and chicken, etc.).

In order to measure the level of a disease associated miRNA or variant there of, a method known in the art to measure nucleic acid expression may be used. For example, the expression level of a disease-associated miRNA may be measured by contacting a biological sample with a probe or biochip and measuring the amount of hybridization. An miRNA may be measured by standard methods, such as a Northern Blot, Polymerase Chain Reaction, or microarray analysis.

Furthermore, a target nucleic acid may be detected by contacting a sample comprising the target nucleic acid with a biochip comprising an attached probe sufficiently complementary to the target nucleic acid and detecting hybridization to the probe above control levels.

The target nucleic acid may also be detected by immobilizing the nucleic acid to be examined on a solid support such as nylon membranes and hybridizing a labeled probe with the sample. Similarly, the target nucleic may also be detected by immobilizing the labeled probe to the solid support and hybridizing a sample comprising a labeled target nucleic acid. Following washing to remove the non-specific hybridization, the label may be detected.

The target nucleic acid may also be detected in situ by contacting permeabilized cells or tissue samples with a labeled probe to allow hybridization with the target nucleic acid. Following washing to remove the non-specifically bound probe, the label may be detected.

These assays can be direct hybridization assays or can comprise sandwich assays, which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697, each of which is hereby incorporated by reference.

A variety of hybridization conditions may be used, including high, moderate and low stringency conditions as outlined above. The assays may be performed under stringency conditions which allow hybridization of the probe only to the target. Stringency can be controlled by altering a step parameter that is a thermodynamic variable, including, but not limited to, temperature, formamide concentration, salt concentration, chaotropic salt concentration pH, or organic solvent concentration.

Hybridization reactions may be accomplished in a variety of ways. Components of the reaction may be added simultaneously, or sequentially, in different orders. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors and anti-microbial agents may also be used as appropriate, depending on the sample preparation methods and purity of the target.

The activity of the target protein (i.e., the protein encoded by the RNA targeted by the miRNA) or protein pathway may also be interrogated as a method to measure the level or activity of a nucleic acid of the invention. For example, neurofibromin converts Ras from its active GTP to its inactive GDP isoforms. Since there is often a loss of function of neurofibromin in NF1, the Ras signaling pathway will be more active. Thus, a nucleic acid targeted to inhibit the Ras protein or another protein in the Ras pathway could be measured by the level of inhibition observed in Ras signaling. Standard methods known in the art may be used to detect the state of the Ras pathway or other signaling pathways or proteins in the cell, e.g., phosphoELISA™, ELISA, and Western blots may be used. The Ras pathway may be activated by intracellular events or by the binding of factors to receptor tyrosine kinases (RTKs). The Ras pathway promotes proliferation and cell growth and is associated with many cancer types. Activation of the Ras pathway may further be assayed by the detection of phosphorylated Ras (e.g., by ELISA or Westernblot), or, e.g., phosphorylated MEK, ERK, ore Elk-1 which are members of the Ras pathway.

In addition, other methods known in the art for detecting miRNA may be employed. For example, the methods described in U.S. Pat. Pub. Nos. US20060292616A1, US 2006/0228729, and US 2007/0050146 (which are all incorporated herein by reference in their entirety) may be used.

B. Gene Silencing

The present invention relates, in part, to a method of using the nucleic acids of the invention to reduce expression of a target gene, e.g., NF1, in a cell, tissue or organ. Expression of the target gene may be reduced by expressing a nucleic acid of the invention that comprises a sequence substantially complementary to one or more binding sites of the target mRNA. The nucleic acid may be a miRNA or a variant thereof. The nucleic acid may also be pri-miRNA, pre-miRNA, or a variant thereof, which may be processed to yield an miRNA. The expressed miRNA may hybridize to a substantially complementary binding site on the target mRNA, which may lead to translational repression or activation of RISC-mediated gene silencing.

The target of gene silencing may also be a gene or protein that causes the silencing of a second gene or protein. By repressing expression of the target gene, expression of the second protein may be increased. Examples for efficient suppression of miRNA expression are the studies by Esau et al 2004 JBC 275-52361; and Cheng et al 2005 Nucleic Acids Res. 33-1290, which are incorporated herein by reference.

C. Gene Enhancement

The present invention also relates to a method of using the nucleic acids of the invention to increase expression of a target gene in a cell, tissue or organ. Expression of the target gene may be increased by expressing a nucleic acid of the invention that comprises a sequence substantially complementary to a pri-miRNA, pre-miRNA, miRNA or a variant thereof. The nucleic acid may be an anti-miRNA. The anti-miRNA may hybridize with a pri-miRNA, pre-miRNA or miRNA, thereby reducing its gene repression activity. Expression of the target gene may also be increased by expressing a nucleic acid of the invention that is substantially complementary to a portion of the binding site in the target gene, such that binding of the nucleic acid to the binding site may prevent miRNA binding.

Alternatively, an miRNA may be used to increase gene expression. Recent evidence has shown that an miRNA may

D. Treating NF-1 Related Pathologies

The present invention also relates to a method of using the nucleic acids of the invention, e.g., miRNAs (e.g., let-7a, pre-let7a, miR10a, pre-miR10a, miR-137, pre-miR-137, miR-490, pre-miR-490, miR-10b, pre-miR-10b, miR-155, pre-miR155, and/or miR-355, pre-miR355), as modulators of NF1-related pathologies and disease. In general, the claimed nucleic acid molecules may be used as a modulator of the level of gene products from genes which are at least partially complementary to said nucleic acid.

In a further preferred embodiment, miRNA molecules may act as a therapeutic target, e.g., when it is desirable to inhibit the miRNA in order to treat the disease or a symptom thereof. For example, in one embodiment, inhibiting the level of miR-10b or pre-miR10b may slow or prevent NF1-related tumors, tumorigenesis and/or tumor progression. In another embodiment, inhibiting miR-335 or pre-miR355 may slow tumor growth. In another embodiment, enhancing the level of let7a expression may slow tumor growth. In one embodiment, a combination therapy in which agents that modulate more than one of the agents described herein may be employed.

Furthermore, existing miRNA molecules may be used as starting materials for the manufacture of sequence-modified miRNA molecules, in order to modify the target-specificity thereof, e.g. an oncogene, a multidrug-resistance gene or another therapeutic target gene. Further, miRNA molecules can be modified, in order that they are processed and then generated as double-stranded siRNAs which are again directed against therapeutically relevant targets. Furthermore, miRNA molecules may be used for tissue reprogramming procedures, e.g. a differentiated cell line might be transformed by expression of miRNA molecules into a different cell type or a stem cell.

Accordingly, in another aspect, the invention provides therapeutics for the treatment of NF1, NF1-related pathologies, and NF1-related tumors. In one embodiment the invention provides methods of treating a subject having NF1, for example, by administering to the subject an effective amount of an agent which modulates the level of at least one miRNA gene product in a target cell. In some embodiments the agent is an miR-10b inhibitor and/or a let-7a enhancer.

In one embodiment, the level of a target gene product may be reduced indirectly. For example, on one embodiment, the level of the TWIST1 gene product may be reduced to indirectly downmodulate miR-10b. In another embodiment, the activity of the TWIST1 gene product may be reduced to downmodulate miR-10b. In such embodiments of the invention, methods known in the art may be used to alter the level of the level or activity of the TWIST1 gene product.

The present invention also provides a method of identifying an agent that ameliorates at least one sign or symptom associated with a NF1-related tumor, leukemia and/or other NF1-related pathologies, comprising (i) contacting a cell with a test agent, (ii) measuring the effect of the test agent on the level TWIST1 in the cell, wherein an alteration in the level of TWIST1 in the cell relative to an appropriate control identifies the test agent as one which ameliorates at least one sign or symptom associated with NF1-related tumor, leukemia or other NF1-related pathologies. One of skill in the art will understand that the level of TWIST1 may be a gene expression level, an mRNA level, a protein expression level, or a protein activity level, as measured by methods well known in the art.

In another embodiment the invention provides methods of treating a subject having or at risk for developing NF1-related tumor, leukemia and/or other NF1-related pathologies comprising, administering to the subject an effective amount of an agent which modulates the level of at least one miRNA gene product in a target cell. In some embodiments the agent is a miR-490 inhibitor and/or a miR-137 inhibitor.

As used herein, "an agent which modulates the level of at least one miRNA gene product" indicates that the agent, when administered to a sample or subject increases or a decreases in the measured value of at least one miRNA. In some embodiments the miRNA is increased or decreased by an amount between 1-fold and 20-fold, or more than 20-fold. In some particular embodiments the miRNA is increased or decreased by 1-fold, 2-fold, 3-fold, 4-fold, 5-fold, 7-fold, 9-fold, 10-fold, 12-fold, or 15-fold, or more. In other embodiments the miRNA is increased or decreased by 5%, 10%, 20%, 30%, 40%, 50%, 60%, 70%, 80%, 90%, 100%, 150%, 200%, 300%, or more.

In one embodiment, an "agent" which can increase or decrease the level of an miRNA or variant thereof (including a pri-miRNA or pre-miRNA) may be a non-nucleic acid agent, e.g., an antibody or antigen binding fragment thereof (including a Fab fragment, a $F(ab')_2$ fragment, a single chain Fv fragment, an SMIP, an affibody, an avimer, a nanobody, and a single domain antibody), a small molecule, a peptide therapeutic, an aptamer, etc.

Improvement in NF1 and/or NF1-tumor or NF1-related pathology may be measured by any methods known in the art. In one embodiment an improvement is shown if the subject exhibits fewer or reduced signs or symptoms of NF1 or NF1-related tumor. In another embodiment, and an improvement can be measured by measuring the amount of various miRNAs. For example, when an miRNA has an altered expression level in a subject having NF1 or NF1-related tumor, an improvement may exist if the miRNA expression level returns to that found in a control subject or a subject which does not have NF1 or other NF1-related pathology, e.g., an NF1-related tumor. Other measures may also be used, e.g., a reduction in tumor size, a reduction in the size or number of neurofibromas, a prevention of the formation of neurofibromas, a prevention or delay in the onset of cognitive deficits, a delay or prevention of NF1 progression (e.g., when NF1-related tumors take longer to develop or develop more slowly in treated subjects as compared to control or normal subjects), etc.

In a fourth aspect, the invention provides therapeutics for the treatment of cognitive deficits. The invention provides methods to ameliorate cognitive defects in a juvenile subject with NF1, NF1-related tumor, leukemia, and/or other NF1-related pathologies comprising, administering to the subject an effective amount of an agent which decreases the level of the miR-10 gene miRNA gene product in a target cell. In some embodiments it may be desirable to decrease the level of miR-10a, miR-10b, or miR-155, pre-miR155, miR-355, pre-miR355, or to increase the level of let7a in order to treat a cognitive deficit.

The effectiveness of a treatment for a cognitive deficit can be determined by a history of improved job performance; better organization; improved goal selection, planning and attainment. The effectiveness of a treatment for a cognitive deficit can also be determined from various standardized tests, such as the Cambridge Neuropsychological Test Automated Battery (CANTAB), which is sensitive to executive function deficits and can report a variety of cognitive impairments, including spatial short-term memory, spatial working memory, set-shifting ability, planning ability, spatial recognition memory, delayed matching to sample, and pattern recognition memory. Accordingly, the treatments described herein for treating cognitive deficits should improve a subject's performance on such tests or in such criteria.

According to one aspect of the invention, the level of a plurality of gene products in a subject may be modulated by administering, to the subject, a composition such as the nucleic acids that are substantially antisense to an miRNA, or a sequence that, when expressed by the cell, causes the cell to overexpress the miRNA (e.g., a DNA sequence encoding an miRNA such that transcription of the DNA initiated in the cell produces an abundance of miRNA), etc. The alteration of the expression of a gene can also be used, according to still another aspect, to treat diseases that are characterized by altered gene expression, for example, cancer or other diseases in which cells reproduce uncontrollably. By administering, to a subject, a composition comprising a nucleic acid of the invention, the expression of a gene involved in cell reproduction can thus be controlled to control cell growth. For instance, as described above, such a method can be used to treat a cancer or a tumor (e.g., NF1-related tumor or cancer). For example, the synthesized nucleic acid may be introduced into a cancer cell. The nucleic acid may then interact with the UTR of a gene sequence within the cancer cell to at least partially inhibit expression of the gene, thereby controlling, or killing, the cancer cell. Thus, one set of embodiments provides systems and methods effecting changes in miRNA levels in cells in vitro or in vivo.

E. Diagnosing and Predicting Bone Disorders

Subjects having NF1 may present with an NF1-related disease or pathology and may have symptoms that include bone disorders, skeletal abnormalities, scoliosis, kyphosis, pseudoarthrosis, bowing of the tibia, and a distinctive bony lesions such as sphenoid dysplasia or thinning of long-bone cortex, with or without pseudoarthrosis.

As used herein, a "bone disorder" includes a bone or skeletal abnormality. In some preferred embodiments the bone disorder is NF1-related bone dysplasia, long bone displasia, tibial dysplasia, skeletal growth defects, scoliosis, bone healing defects, osteopenia, osteoporosis, tooth cementum overgrowth, short angle scoliosis, sphenoid wing dysplasia, decreased bone mineral density, increased osteoclastogenesis, osteomalacia, short stature, macrocephaly, pseudoarthrosis, dystrophic and non-dystrophic spinal curvature, dystrophic scoliosis, dural ectasia, mesodermal dysplasia of the meninges, kyphoscoliosis, weakening of spinal stabilizers (e.g. facets, pedicles, and ligaments), meningocele formation, chest wall deformities, inferior pectus excavatum, superior pectus carinatum, kyphosis, sphenoid wing defects (e.g., arachnoid cysts, dural ectasia or buphthalmos), cystic osseous lesions, dental abnormalities, bone overgrowth, bone erosion, bone distortion, ossifying subperiosteal hematomas, increased bone porosity, and decreased bone calcium content. In some preferred embodiments the bone disorder is scoliosis or spinal abnormalities. In other preferred embodiments the bone disorder is kyphosis, arthritis, or pseudoarthritis. In other preferred embodiments the bone disorder is a bony lesion. In other embodiments the bone disorder is sphenoid dysplasia, thinning of long-bone cortex, bowing of the tibia, bone aplasia (e.g., bilateral aplasia of the fibula and the radius, aplasia of the ulna), hypoplasia and dislocation of both tibiae, irregularities in carpal bones and fingers, etc. The list above is for the purposes of example and is not limiting in any way.

Accordingly, the present invention includes methods to diagnose or predict whether a subject has, or is at risk for developing a bone disorder. In some embodiments the bone disorder is an NF1-related pathology, e.g., as described above. In some specific embodiments, the bone disorder may be unrelated to NF1.

MiR-10b is located in chromosome 2 (2q31) and is very close to HOXD gene family. Chromosomal breaks at 2q31 have been linked to bone disorders. For example, subjects with chromosomal breaks at 2q31 have presented with bone abnormalities including scoliosis, aplasia of the ulna, shortening of the radius, finger abnormalities, bilateral aplasia of the fibula and the radius, bilateral hypoplasia of the ulna, unossified carpal bones, and hypoplasia and dislocation of both tibiae (see, e.g., Dlugaszewska et al. Journal of Medical Genetics 2006, 43:111-118, incorporated herein by reference).

In some embodiment the invention provides methods to diagnose or predict whether a subject has, or is at risk for developing a bone disorder, comprising (i) measuring in a test sample from the subject the level of at least one miRNA gene product in the test sample, wherein an alteration in the level of miRNA gene product in the test sample relative to the level of corresponding miRNA gene product in a control sample is indicative of the subject either having, or being at risk for developing, a bone disorder. In some embodiments the miRNA gene product is miR-155, pre-miR155, miR-355, pre-miR355, miR-137, pre-miR-137, miR-490, pre-miR-490, miR-10b, and/or pre-miR-10b.

In some embodiments, a subject having or at risk for developing a bone disorder will exhibit altered levels of certain miRNAs. In some embodiments a subject having or at risk for developing a bone disorder has increased levels of miR-10b, miR-490, and/or miR-137. Accordingly, measuring the level or activity of miR-155, pre-miR155, miR-355, pre-miR355, miR-10b, pre-miR-10b, MiR-490, pre-miR-490, miR-137, and/or pre-miR-137 in a subject, and determining one or more are elevated, may indicate that the subject has or is at risk of developing a bone disorder. In some embodiments a subject having or at risk for developing a bone disorder has decreased levels of let-7a and/or let-7b. Accordingly, measuring the level or activity of let-7a and/or let7b in a subject, and determining that it is decreased, may indicate that the subject has or is at risk of developing a bone disorder.

In some specific embodiments, a determination that miR-10b is elevated indicates that the subject has or is at risk of developing scoliosis. In other embodiments, a determination that miR-10b is elevated indicates that the subject has or is at risk of developing kyphosis, pseudoarthrosis, bowing of the tibia, sphenoid dysplasia or bony lesions.

IV. Screening Methods of the Invention

In one embodiment, the invention provides a method for detecting an agent capable of modulating (e.g., up- or down-modulating) the level of at least one miRNA or pre-miRNA in a sample, e.g., a cell (such as a neural cell). The method involves contacting the biological sample or a component(s) derived therefrom (e.g., a cell, a cellular extract, nucleic acid molecules) with an agent capable of detecting at least one miRNA or pre-miRNA molecule or an activity associated therewith or a molecule regulated by a miRNA molecule. Small molecules have recently been found to be capable of regulating miRNAs (Shan et al. 2008. Nature Biotechnology 26:2008), incorporated by reference herein.

A preferred agent for detecting the level of an miRNA or pre-miRNA is a nucleic acid molecule capable of specifically hybridizing to the miRNA or pre-miRNA, a set of primers which can amplify the miRNA or pre-miRNA using methods known in the art.

The invention provides methods for identifying compounds, i.e., candidate or test compounds or agents (e.g., peptidomimetics, small molecules or other drugs) that modulate, the level of at least one miRNA molecule. Modulators of miRNAs can be known (e.g., synthetic miRNA molecules, synthetic DNA molecules can be enhancers for upmodulating miRNA levels, or antigomirs which are complementary to miRNA molecules can be used to inhibit or downregulate the level of at least one miRNA molecule) or can be identified using the methods described herein or other methods know to the skilled artisan.

In one embodiment, the invention pertains to a method of identifying an agent that increases neurofibromin expression in a cell, comprising (i) contacting a cell with a test agent, (ii) measuring the effect of the test agent on the level of at least one miRNA gene product in the cell, wherein an alteration in the level of the at least one miRNA gene product in the cell relative to an appropriate control identifies the test agent as one which increases neurofibromin expression, wherein the at the at least one miRNA gene product is selected from the group consisting of miR-10b and pre-miR-10b. In one embodiment, the method further comprises measuring neurofibromin expression. In another embodiment, the method further comprises measuring the ability of the test compound to ameliorate at least one sign or symptom associated with NF1 or NF1-related pathologies.

In another embodiment, the invention pertains to a method of identifying an agent that ameliorates at least one sign or symptom associated with NF1 (or NF1-related pathologies), comprising (i) contacting a cell with a test agent, (ii) measuring the effect of the test agent on the level of at least one miRNA gene product in the cell, wherein an alteration in the level of the at least one miRNA gene product in the cell relative to an appropriate control identifies the test agent as one which ameliorates at least one sign or symptom associated with NF1 (or NF1-related pathologies), wherein the at least one miRNA gene product is selected from the group consisting of miR-10b, pre-miR-10b, miR-355, pre-miR355, let-7a, and pre-let7a.

In one embodiment, the level of a miR-10-b gene product is measured and the method further comprises measuring neurofibromin expression in the cell. Neurofibromin expression can be measured as described herein or using methods known in the art. Its expression can be measured by looking at levels of transcription of the gene or at levels of the protein.

In one embodiment, the level of a let-7a gene product is measured and the method further comprises measuring Ras signaling pathway in the cell. Activation of the Ras signaling pathway can be measured as described herein, or using methods known to those of skill in the art.

In one embodiment, the invention pertains to a method of identifying an agent that ameliorates at least one sign or symptom associated with NF1, e.g., an NF1 tumor, leukemia and/or other NF1-related pathologies, comprising (i) contacting a cell with a test agent, (ii) measuring the effect of the test agent on the level of at least one miRNA gene product in the cell, wherein an alteration in the level of the at least one miRNA gene product in the cell relative to an appropriate control identifies the test agent as one which ameliorates at least one sign or symptom associated with NF1, e.g., an NF1 tumor, leukemia and/or NF1-related pathologies, wherein the at least one miRNA gene product is selected from the group consisting of miR-137, pre-miR-137, miR-355, pre-miR355, miR-490, and pre-miR-490.

Compounds identified using the assays described herein may be useful for treating NF1 (or NF1-related pathologies) or treating at least one sign or symptom associated with the disease, e.g., one or more signs or symptoms described herein, such as, cognitive disorders, bone disorders, NF-associated tumors, hyperpigmented macules, neurofibromas, optic glioma, Lisch nodules (iris hamartomas), and sphenoid dysplasia, or thinning of long-bone cortex.

In another aspect, the invention pertains to a combination of two or more of the assays described herein. For example, a modulating agent can be identified using a cell-based assay and can be confirmed in vivo, e.g., in an animal.

A variety of test compounds can be evaluated using the screening assays described herein. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909) peptoids (Zuckermann. (1994). *J. Med. Chem.* 37:2678) oligocarbamates (Cho et al. (1993). *Science.* 261:1303-), and hydantoins (DeWitt et al. supra). An approach for the synthesis of molecular libraries of small organic molecules with a diversity of 104-105 as been described (Carell et al. (1994). *Angew. Chem. Int. Ed. Engl.* 33:2059-; Carell et al. (1994) *Angew. Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Compound Des.* 12:145). Other exemplary methods for the synthesis of molecular libraries can be found in the art, for example in: Erb et al. (1994). *Proc. Natl. Acad. Sci. USA* 91:11422-; Horwell et al. (1996) *Immunopharmacology* 33:68-; and in Gallop et al. (1994); *J. Med. Chem.* 37:1233-.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant or inactive forms of miRNA molecules, e.g., dominant negative mutant forms of the molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Compound Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

Compounds identified in the subject screening assays can be used in methods of modulating one or more of the biological responses regulated by the NF1 gene or the miRNA molecules described herein. It will be understood that it may be desirable to formulate such compound(s) as pharmaceutical compositions (described supra) prior to contacting them with cells.

Once a test compound is identified that directly or indirectly modulates an miRNA expression and/or activity, by one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response). Compounds of interest can also be identified using structure based drug design using techniques known in the art.

The instant invention also pertains to compounds identified in the above assays.

V. Pharmaceutical Compositions and Delivery Methods

A. Pharmaceutical Compositions

In another aspect, the present invention provides a composition, e.g., a pharmaceutical composition, containing one or more nucleic acids, e.g., miRNAs produced by the methods of the invention, formulated together with a pharmaceutically acceptable carrier. Pharmaceutical compositions of the invention also can be administered in combination therapy, i.e., combined with other agents. For example, the combination therapy can include a protein of the present invention combined with at least one other anti-cancer agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the protein or variant thereof of the invention, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Exemplary formulations comprise at least one miRNA of the invention and can comprise lower concentrations of stabilizing (or disaggregation) agents which can, in addition to the methods disclosed herein, be used to prevent or diminish aggregation of a nucleic acid. Accordingly, conventional methods used to prevent aggregation may be employed in the development of pharmaceutical compositions containing nucleic acids produced by the methods of the present invention. For example, a variety of stabilizing or disaggregating compounds may be included in pharmaceutical compositions of the invention depending on their intended use and their biological toxicity. Such stabilizing compounds may include, for example, cyclodextrin and its derivatives (U.S. Pat. No. 5,730,969), alkylglycoside compositions (U.S. patent application Ser. No. 11/474,049), betaine compounds (Xiao, Burn, Tolbert, Bioconjug Chem. 2008 May 23), surfactants (e.g., Pluronic F127, Pluronic F68, Tween 20 (Wei et al. International Journal of Pharmaceutics. 2007, 338(1-2):125-132))

In addition, nucleic acids may be stabilized in formulations using combinations of different classes of excipients, e.g., (1) disaccharides (e.g. Saccharose, Trehalose) or polyols (e.g. Sorbitol, Mannitol) act as stabilizers by preferential exclusion and are also able to act as cryoprotectants during lyophilization, (2) surfactants (e.g. Polysorbat 80, Polysorbat 20) act by minimizing interactions of interfaces on interfaces like liquid/ice, liquid/material-surface and/or liquid/air interfaces and (3) buffers (e.g. phosphate-, citrate-, histidine) help to control and maintain formulation pH. Accordingly, such disaccharides polyols, surfactants and buffers may be used in addition to the methods of the present invention to further stabilize nucleic acids and prevent their aggregation.

Pharmaceutical compositions of the invention may also include chelating agents (e.g., EDTA) and/or proteinases or other substances to inactivate DNAses or RNAses and stabilize nucleic acid compositions. In other embodiments, the pharmaceutical composition may be formulated to enable protein stability and prevent protein aggregation, e.g., when an miRNA or miRNA encoding vector is transmitted via virus. The solvents and stabilizing agents described in U.S. Pat. Nos. 6,271,206; 6,271,208; 5,547,932; 5,981,273; 5,854,224; 5,705,188; and U.S. application Ser. No. 10/568,101, which are all incorporated herein by reference.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the nucleic acid, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for a protein of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively a nucleic acid of the invention can be administered as a sustained release formulation, in which case less frequent administration is required. Dosage and frequency vary depending on the half-life of the administered substance in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of signs or symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of nucleic acid (e.g., miRNA) of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

As previously described, the nucleic acids of the invention can be co-administered with one or other more therapeutic agents, e.g., an miRNA inhibitor, an miRNA enhancer, a small molecule, a cytotoxic agent, a radiotoxic agent, a chemotherapeutic agent, or an immunosuppressive agent. The nucleic acid can be linked to the agent or can be administered separate from the agent. In the latter case (separate administration), the nucleic acid can be administered before, after or concurrently with the additional therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of a nucleic acid of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the binding moiety. In general, the term "anti-tumor therapeutic" as used herein may include the agents mentioned above, other chemotherapeutic agents, and, in some embodiments, the nucleic acids of the invention.

B. Administration and Delivery Methods

A composition of the present invention can be administered via one or more routes of administration using one or more of a variety of methods known in the art. As will be appreciated by the skilled artisan, the route and/or mode of administration will vary depending upon the desired results. Preferred routes of administration for binding moieties of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, nucleic acid, e.g., miRNA of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Binding or other association of the miRNA to the target mRNA sequence may occur through limited base-pairing interactions with a complementary site within the UTR of the target mRNA sequence, for example, through Watson-Crick ("W-C") complementarity pairs (A:U and C:G pairing) (i.e., "perfect" complementarity) and/or G:U pairing. The pairing may also be to a coding portion of an mRNA sequence in some cases, i.e., to a portion of an mRNA which is expressed (e.g., as a protein), i.e. that portion that encodes one or more amino acids that are expressed as a protein or a peptide, etc. Thus, it should be understood that the discussions herein with respect to binding of miRNAs to UTRs of mRNAs is by way of example only, and in other embodiments of the present invention, certain miRNAs may bind to coding portions of the mRNA, and/or both the coding portions and the UTR portions of the mRNA.

Some methods of the invention involve binding of an oligonucleotide to an miRNA or mRNA. In some cases, a portion of the oligonucleotide binds to the complementary site within the UTR of the target mRNA or within the miRNA. The portion may have perfect complementarity with the mRNA or miRNA sequence, i.e., through Watson-Crick complementarity pairing, and the portion may be 5, 6, 7, 8, 9, 10, 11, 12, or more nucleotides long. Longer portions are also possible in some instances. In other cases, however, the complementary region between the miRNA or UTR of the mRNA and the oligonucleotide portions may also include G:U pairings in addition to Watson-Crick complementarity pairing.

Thus, regardless of the particular pharmaceutical formulation, the invention involves delivery to cells of isolated nucleic acids, including but not limited to oligonucleotides that are substantially antisense to at least a portion of an mRNA, oligonucleotides that comprise an miRNA sequence (e.g., oligonucleotides having stem-loop structures or miRNA duplexes) and/or expression vectors that encode miRNA sequences. Any method or delivery system may be used for the delivery and/or transfection of the nucleic acids, and such delivery and/or transfection may occur in vitro or in vivo. If in vivo, the cell may be in a subject, for example, a human or non-human mammal, such as a monkey, ape, cow, sheep, goat, buffalo, antelope, oxen, horse, donkey, mule, deer, elk, caribou, water buffalo, camel, llama, alpaca, rabbit, pig, mouse, rat, guinea pig, hamster, dog, cat, etc. The oligonucleotide, or the nucleotide sequence able to be transcribed to produce the oligonucleotide, may be delivered to the cell alone, or in combination with other agents. Examples of delivery systems include, but are not limited to, particle gun technology, colloidal dispersion systems, electroporation, vectors, and the like. In its broadest sense, a "delivery system," as used herein, is any vehicle capable of facilitating delivery of a nucleic acid (or nucleic acid complex) to a cell and/or uptake of the nucleic acid by the cell. Other non-limiting example delivery systems that can be used to facilitate uptake by a cell of the nucleic acid include calcium phosphate or other chemical mediators of intracellular transport, microinjection compositions, or homologous recombination compositions (e.g., for integrating a gene into a predetermined location within the chromosome of the cell).

The term "transfection," as used herein, refers to the introduction of a nucleic acid into a cell, for example, miRNA, or a nucleotide sequence able to be transcribed to produce miRNA. Transfection may be accomplished by a wide variety of means, as is known to those of ordinary skill in the art. Such methods include, but are not limited to, Agrobacterium-mediated transformation (e.g., Komari, et al., Curr. Opin. Plant Biol., 1:161 (1998)), particle bombardment mediated transformation (e.g., Finer, et al., Curr. Top. Microbiol. Immunol., 240:59 (1999)), protoplast electroporation (e.g., Bates, Methods Mol. Biol., 111:359 (1999)), viral infection (e.g., Porta and Lomonossoff, Mol. Biotechnol. 5:209 (1996)), microinjection, and liposome injection. Standard molecular biology techniques are common in the art (e.g., Sambrook, et al., Molecular Cloning: A Laboratory Manual, 2.sup.nd ed., Cold Spring Harbor Laboratory Press, New York (1989)). For example, in one embodiment of the present invention, a mammalian cell or other vertebrate cell is transformed with a gene encoding an oligonucleotide comprising a sequence that is substantially antisense to an miRNA, or a sequence able to be transcribed to produce an oligonucleotide comprising a sequence that is substantially antisense to an miRNA.

In one set of embodiments, genetic material may be introduced into a cell using particle gun technology, also called microprojectile or microparticle bombardment, which involves the use of high velocity accelerated particles. In this method, small, high-density particles (microprojectiles) are accelerated to high velocity in conjunction with a larger, powder-fired macroprojectile in a particle gun apparatus. The microprojectiles have sufficient momentum to penetrate cell walls and membranes, and can carry oligonucleotides into the interiors of bombarded cells. It has been demonstrated that such microprojectiles can enter cells without causing death of the cells, and that they can effectively deliver foreign genetic material into intact tissue.

In another set of embodiments, a colloidal dispersion system may be used to facilitate delivery of a nucleic acid (or nucleic acid complex) into the cell, for example, an isolated oligonucleotide that is substantially antisense to an miRNA, a sequence able to be transcribed to produce an oligonucleotide comprising a sequence that is substantially antisense to an miRNA, a sequence that, when expressed by the cell, causes the cell to overexpress the miRNA, etc. As used herein, a "colloidal dispersion system" refers to a natural or synthetic molecule, other than those derived from bacteriological or viral sources, capable of delivering to and releasing the nucleic acid to the cell. Colloidal dispersion systems include, but are not limited to, macromolecular complexes, beads, and lipid-based systems including oil-in-water emulsions, micelles, mixed micelles, and liposomes. One example of a colloidal dispersion system is a liposome. Liposomes are artificial membrane vessels. It has been shown that large unilamellar vessels ("LUV"), which can range in size from 0.2 to 4.0 micrometers, can encapsulate large macromolecules within the aqueous interior and these macromolecules can be delivered to cells in a biologically active form (e.g., Fraley, et al., Trends Biochem. Sci., 6:77 (1981), incorporated herein by reference).

Lipid formulations for the transfection and/or intracellular delivery of nucleic acids are commercially available, for instance, from QIAGEN, for example as EFFECTENE™ (a non-liposomal lipid with a special DNA condensing enhancer) and SUPER-FECT™ (a novel acting dendrimeric technology) as well as Gibco BRL, for example, as LIPO-FECTIN™ and LIPOFECTACE™, which are formed of cationic lipids such as N-[4-(2,3-dioleyloxy)-propyl]-N,N,N-trimethylammonium chloride ("DOTMA") and dimethyl dioctadecylammonium bromide ("DDAB"). Liposomes are well known in the art and have been widely described in the literature, for example, in Gregoriadis, G., Trends in Biotechnology 3:235-241 (1985).

Electroporation may be used, in another set of embodiments, to deliver a nucleic acid (or nucleic acid complex) to the cell, e.g., an isolated oligonucleotide that is substantially antisense to an miRNA, a sequence able to be transcribed to produce an oligonucleotide comprising a sequence that is substantially antisense to an miRNA, a sequence that, when expressed by the cell, causes the cell to overexpress the miRNA, etc. "Electroporation," as used herein, is the application of electricity to a cell in such a way as to cause delivery of a nucleic acid into the cell without killing the cell. Typically, electroporation includes the application of one or more electrical voltage "pulses" having relatively short durations (usually less than 1 second, and often on the scale of milliseconds or microseconds) to a media containing the cells. The electrical pulses typically facilitate the non-lethal transport of extracellular nucleic acids into the cells. The exact electroporation protocols (such as the number of pulses, duration of pulses, pulse waveforms, etc.), will depend on factors such as the cell type, the cell media, the number of cells, the substance(s) to be delivered, etc., and can be determined by those of ordinary skill in the art.

In yet another set of embodiments, a nucleic acid (e.g., an isolated oligonucleotide that is substantially antisense to an miRNA or a mRNA UTR, a sequence able to be transcribed to produce an oligonucleotide comprising a sequence that is substantially antisense to an miRNA, a sequence that, when expressed by the cell, causes the cell to overexpress the miRNA, etc.) may be delivered to the cell in a vector. In its broadest sense, a "vector" is any vehicle capable of facilitating the transfer of the nucleic acid to the cell such that the nucleic acid can be processed and/or expressed in the cell. The vector may transport the nucleic acid to the cells with reduced degradation, relative to the extent of degradation that would result in the absence of the vector. The vector optionally includes gene expression sequences or other components able to enhance expression of the nucleic acid within the cell. The invention also encompasses the cells transfected with these vectors, including cells such as those previously described.

In general, vectors useful in the invention include, but are not limited to, plasmids, phagemids, viruses, other vehicles derived from viral or bacterial sources that have been manipulated by the insertion or incorporation of the nucleotide sequences (or precursor nucleotide sequences) of the invention. Viral vectors useful in certain embodiments include, but are not limited to, nucleic acid sequences from the following viruses: retroviruses such as Moloney murine leukemia viruses, Harvey murine sarcoma viruses, murine mammary tumor viruses, and Rouse sarcoma viruses; adenovirus, or other adeno-associated viruses; SV40-type viruses; polyoma viruses; Epstein-Barr viruses; papilloma viruses; herpes virus; vaccinia virus; polio viruses; or RNA viruses such as retroviruses. One can readily employ other vectors not named but known to the art. Some viral vectors can be based on non-cytopathic eukaryotic viruses in which non-essential genes have been replaced with the nucleotide sequence of interest. Non-cytopathic viruses include retroviruses, the life cycle of which involves reverse transcription of genomic viral RNA into DNA with subsequent proviral integration into host cellular DNA.

Genetically altered retroviral expression vectors may have general utility for the high-efficiency transduction of nucleic acids. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the cells with viral particles) are well known to those of ordinary skill in the art. Examples of standard protocols can be found in Kriegler, M., Gene Transfer and Expression, A Laboratory Manual, W. H. Freeman Co., New York (1990), or Murry, E. J. Ed., Methods in Molecular Biology, Vol. 7, Humana Press, Inc., Cliffton, N.J. (1991).

Another example of a virus for certain applications is the adeno-associated virus, which is a double-stranded DNA virus. The adeno-associated virus can be engineered to be replication-deficient and is capable of infecting a wide range of cell types and species. The adeno-associated virus further has advantages, such as heat and lipid solvent stability; high transduction frequencies in cells of diverse lineages; and/or lack of superinfection inhibition, which may allow multiple series of transductions.

Another vector suitable for use with the invention is a plasmid vector. Plasmid vectors have been extensively described in the art and are well-known to those of skill in the art. See, e.g., Sambrook, et al., Molecular Cloning: A Laboratory Manual, Second Edition, Cold Spring Harbor Laboratory Press, 1989. These plasmids may have a promoter compatible with the host cell, and the plasmids can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom-designed, for example, using restriction enzymes and ligation reactions, to remove and add specific fragments of DNA or other nucleic acids, as necessary. The present invention also includes vectors for producing nucleic acids or precursor nucleic acids containing a desired nucleotide sequence (which can, for instance, then be cleaved or otherwise processed within the cell to produce a precursor miRNA). These vectors may include a sequence encoding a nucleic acid and an in vivo expression element, as further described below. In some cases, the in vivo expression element includes at least one promoter.

The nucleic acid, in one embodiment, may be operably linked to a gene expression sequence which directs the expression of the nucleic acid within the cell (e.g., to produce an oligonucleotide that is substantially antisense to an miRNA, or a sequence able to be transcribed to produce an oligonucleotide comprising a sequence that is substantially antisense to an miRNA). The nucleic acid sequence and the gene expression sequence are said to be "operably linked" when they are covalently linked in such a way as to place the transcription of the nucleic acid sequence under the influence or control of the gene expression sequence. A "gene expression sequence," as used herein, is any regulatory nucleotide sequence, such as a promoter sequence or promoter-enhancer combination, which facilitates the efficient transcription and translation of the nucleotide sequence to which it is operably linked. The gene expression sequence may, for example, be a eukaryotic promoter or a viral promoter, such as a constitutive or inducible promoter. Promoters and enhancers consist of short arrays of DNA sequences that interact specifically with cellular proteins involved in transcription, for instance, as discussed in Maniatis, et al., Science 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). In some embodiments, the nucleic acid is linked to a gene expression sequence which permits expression of the nucleic acid in a vertebrate cell. A sequence which permits expression of the nucleic acid in a cell is one which is selectively active in the particular cell and thereby causes the expression of the nucleic acid in those cells. Those of ordinary skill in the art will be able to easily identify promoters that are capable of expressing a nucleic acid in a cell based on the type of cell.

The selection of a particular promoter and enhancer depends on what cell type is to be used and the mode of delivery. For example, a wide variety of promoters have been isolated from plants and animals, which are functional not only in the cellular source of the promoter, but also in numerous other species. There are also other promoters (e.g., viral and Ti-plasmid) which can be used. For example, these promoters include promoters from the Ti-plasmid, such as the octopine synthase promoter, the nopaline synthase promoter, the mannopine synthase promoter, and promoters from other open reading frames in the T-DNA, such as ORF7, etc.

Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

Thus, a variety of promoters and regulatory elements may be used in the expression vectors of the present invention. For example, in some embodiments, an inducible promoter is used to allow control of nucleic acid expression through the presentation of external stimuli (e.g., environmentally inducible promoters). The timing and amount of nucleic acid expression can be controlled in some cases. Non-limiting examples of expression systems, promoters, inducible promoters, environmentally inducible promoters, and enhancers are well known to those of ordinary skill in the art. Non-limiting examples include those described in International Patent Application Publications WO 00/12714, WO 00/11175, WO 00/12713, WO 00/03012, WO 00/03017, WO 00/01832, WO 99/50428, WO 99/46976 and U.S. Pat. Nos. 6,028,250, 5,959,176, 5,907,086, 5,898,096, 5,824,857, 5,744,334, 5,689,044, and 5,612,472, each of which are incorporated herein by reference in their entirety.

As used herein, an "expression element" can be any regulatory nucleotide sequence, such as a promoter sequence or promoter-enhancer combination, which facilitates the efficient expression of a nucleic acid, for example, an isolated nucleic acid that is substantially antisense to an miRNA, a sequence able to be transcribed to produce an oligonucleotide comprising a sequence that is substantially antisense to an miRNA, a sequence that, when expressed by the cell, causes the cell to overexpress the miRNA, etc. The expression element may, for example, be a mammalian or viral promoter, such as a constitutive or inducible promoter. Constitutive mammalian promoters include, but are not limited to, polymerase promoters as well as the promoters for the following genes: hypoxanthine phosphoribosyl transferase ("HPTR"), adenosine deaminase, pyruvate kinase, and alpha-actin. Exemplary viral promoters which function constitutively in eukaryotic cells include, for example, promoters from the simian virus, papilloma virus, adenovirus, human immunodeficiency virus, Rous sarcoma virus, cytomegalovirus, the long terminal repeats of Moloney leukemia virus and other retroviruses, and the thymidine kinase promoter of herpes simplex virus. Other constitutive promoters are known to those of ordinary skill in the art. Promoters useful as expression elements of the invention also include inducible promoters. Inducible promoters are expressed in the presence of an inducing agent. For example, a metallothionein promoter can be induced to promote transcription in the presence of certain metal ions. Other inducible promoters are known to those of ordinary skill in the art. The in vivo expression element can include, as necessary, 5' non-transcribing and 5'0 non-translating sequences involved with the initiation of transcription, and can optionally include enhancer sequences or upstream activator sequences.

Using any gene transfer technique, such as the above-listed techniques, an expression vector harboring a nucleic acid may be transformed into a cell to achieve temporary or prolonged expression. Any suitable expression system may be used, so long as it is capable of undergoing transformation and expressing of the precursor nucleic acid in the cell. In one embodiment, a pET vector (Novagen, Madison, Wis.), or a pBI vector (Clontech, Palo Alto, Calif.) is used as the expression vector. In some embodiments an expression vector further encoding a green fluorescent protein ("GFP") is used to allow simple selection of transfected cells and to monitor expression levels. Non-limiting examples of such vectors include Clontech's "Living Colors Vectors" pEYFP and pEYFP-C1.

In some cases, a selectable marker may be included with the nucleic acid being delivered to the cell. As used herein, the term "selectable marker" refers to the use of a gene that encodes an enzymatic or other detectable activity (e.g., luminescence or fluorescence) that confers the ability to grow in medium lacking what would otherwise be an essential nutrient. A selectable marker may also confer resistance to an antibiotic or drug upon the cell in which the selectable marker is expressed. Selectable markers may be "dominant" in some cases; a dominant selectable marker encodes an enzymatic or other activity (e.g., luminescence or fluorescence) that can be detected in any cell or cell line.

Optionally, germ line cells may be used in the methods described herein rather than, or in addition to, somatic cells. The term "germ line cells" refers to cells in the organism which can trace their eventual cell lineage to either the male or female reproductive cells of the organism. Other cells, referred to as "somatic cells" are cells which do not directly give rise to gamete or germ line cells. Somatic cells, however, also may be used in some embodiments.

Thus, the alteration of the expression of a gene can be used, according to one set of embodiments, to systematically inhibit or express a gene within a cell in vitro, in vivo, or ex vivo, for example, by administering a composition such as an isolated oligonucleotide comprising a sequence that is substantially antisense to an miRNA of the cell. Thus, as an example, a normal cell may be rendered cancerous through the addition of an isolated oligonucleotide comprising a sequence that is substantially antisense to an miRNA of the cell, then rendered non-cancerous by not adding the oligonucleotide, i.e., stopping administration of the oligonucleotide. Tight control of the cancerous/non-cancerous behavior of a cell is a highly useful model of disease function and behavior.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

Introduction to the Examples

Example 1

The bioinformatics software system, TargetScan (targetscan.org/) was used to analyze the 3'UTR of the NF1 gene. The following miRNAs were predicted to possibly target the NF1 3'UTR: miRNAs 107, 137, 30, 490, 10, 128. Real-time quantitative polymerase chain reaction was then to examine the expression levels of these miRNAs in two paired cell lines. The first paired cell lines were human MPNST: STS26T vs. ST8814 and T265. STS26T came from non-NF1-related MPNST and expressed normal NF1 protein and retained normal Ras signaling. ST8814 and T265 came from NF1-related MPNST and expressed very low levels of NF1 protein and showed enhanced Ras signaling. It was found that miR-10b, 137, 490 were over-expressed in NF1 Schwann tumor cell lines (ST8814 and T265) (FIG. 1), compared to non-NF1 Schwann tumor cell lines (STS26T). The level of MiR-10b was found to be 20-30 fold higher. MiR-137 was found to be 5 fold higher. The level of MiR-490 was found to be about 20-70 fold higher. It was also found that the level of let-7a was reduced by half in NF1 Schwann tumor cell lines (FIG. 1). However, miR-10a, miR-30b and 107 expression were similar between NF1 Schwann tumor cell lines and non-NF1 Schwann tumor cell lines (FIG. 1).

The second paired cell lines were mouse embryonic stem (ES) cells: Nf1 wildtype (Nf1+/+) ES cells vs. Nf1 knockout (Nf1−/−) ES cells. Nf1+/+ ES cells expressed normal NF1 protein and exhibited normal levels of Ras signaling. Nf1−/− ES cells expressed very low amounts of NF1 protein and exhibited enhanced Ras signaling. Similar to NF1 MPNST cell lines, Nf1−/− ES cells showed higher expression of miR-10b, lower expression of let-7a, and no change in miR-30b (FIG. 2). Higher levels of miR-10a were also found, and there was no change in miR-490 expression in Nf1−/− ES cells (FIG. 2). The findings are summarized in Table 1 below.

TABLE 1

| | miR-10b | miR-10a | Let-7a | miR-137 | miR-30b | miR-490 | miR-107 |
|---|---|---|---|---|---|---|---|
| NF1 MPNST Cells | ↑↑↑ | ± | ↓ | ↑ | ± | ↑↑↑ | ± |
| Nf1−/− ES Cells | ↑↑↑ | ↑↑↑ | ↓ | ± | ± | ± | ± |

± No change
↑↑↑ Increase
↓ Decrease

Since similar results were found for miR-10b and let-7a in human NF1 MPNST cell lines as well as mouse Nf1−/− ES cells (both cell lines characterized as loss of function at NF1), it was concluded that miR-10b and let-7a were NF1 specific miRNAs. It was also concluded that miR-137 and miR-490 were NF1 tumor specific miRNAs, miR-10a was ES cells specific miRNAs. The target sites in NF1 3'UTR for these miRNAs were listed in FIG. 3.

Examples 2-7

Materials and Methods for Examples 2-7

All human tissues used in this study were obtained under human subject protocols approved by the Institutional Review Boards of the donor institutions and the Maine Institute for Human Genetics & Health. The informed consent was obtained from each subject or subject's guardian. Normal and neurofibroma human Schwann cells were obtained from the University of Florida and from The Ohio State University. Human neurofibroma and MPNST tumor tissues were obtained from the Canadian Virtual Tumor Bank.

Cell Culture:
Primary Schwann Cells:

Normal human Schwann cells were isolated from adult sciatic nerves, procured from the LifeLine of Ohio. NF1 Schwann cells were isolated from NF1 neurofibromas and plexiform neurofibromas by modifications of methods described previously (Jacob, et al. Otol Neurotol 2008. 29:58-68). During subsequent passage, Schwann cells were enriched by differential detachment using mild trypsinization and shaking. All assays were performed using cultures at passage 3 to 4. Before plating cells, dishes were coated with laminin (10 µg/ml in PBS) at 37° C. for 1-2 hr. Coated dishes were rinsed three times with PBS to remove coating components that could interfere with cell division. Cells were then plated in Schwann cell medium containing DMEM, 10% FBS, penicillin (50 IU/ml), streptomycin (50 µg/ml), and neuregulin (50 ng/ml). Fresh medium was replenished every three days neuregulin added each time.

MPNST Cell Lines:

The human NF1 associated MPNST cell lines ST8814 and T265P21, and the non-NF1 associated MPNST cell line STS26T (all kindly supplied by Dr. Nancy Ratner, Cincinnati Children's Hospital Medical Center, Cincinnati, Ohio) were maintained in DMEM medium, supplemented with 10% FBS, 2 mM L-glutamine, penicillin (50 IU/ml), and streptomycin (50 µg/ml).

Analysis of miRNA Expression:

Cells were cultured on 6- or 12-well plates for 24 h, followed by serum starvation in medium containing 0.2% FBS for another 24 h. Frozen neurofibroma and MPNST tumor tissues were homogenized in Trizol with a tissue tearor (BioSpec Products Inc., Bartlesville, Okla.). RNA was extracted from cells or tissues using the RNeasy miRNA kit (Qiagen, Inc., Valencia, Calif.). RNA concentrations were quantified using a Biophotometer spectrophotometer (Eppendorf, Hamburg, Germany).

miRNA Microarray:

Twenty micrograms of total RNA obtained from ST8814 and STS262T were labeled and hybridized on miRNA microarrays (LC Sciences, Houston, Tex.). The arrays were designed to detect miRNA transcripts corresponding to 833 miRNAs included in the Sanger miRBase Release 11.0. Raw signal intensities representing hybridization to probes were mean-normalized across cell lines. Multiple control probes were included in each chip.

Quantitative Real-Time Reverse Transcription-Polymerase Chain Reaction (qRT-PCR):

Reverse transcriptase (RT) and quantitative real-time PCR were performed in a two-step reaction using the Taqman microRNA assays according to protocols provided by the manufacturer (Applied Biosystems, Foster City, Calif.). Quantitative miRNA expression data were acquired and analyzed using an ABI Prism 7500HT Sequence Detection System (Applied Biosystems, Foster City, Calif.). Each RNA sample was analyzed in triplicate. U6 was used as internal control. The $2^{-\Delta\Delta C_T}$ method, described by Livak and Schmitgen (Livak, et al. Methods 2001. 25:402-8), was used to analyze the data.

NF1 3' UTR Reporter Assay:

The 3' UTR of the NF1 gene was amplified from human genomic DNA and its sequence was confirmed by DNA sequencing. The NF1 3' UTR was cloned into the 3'UTR of the pMIR-REPORT™ miRNA Reporter Vector (Ambion, Austin, Tex.). The pMIR reporter vector or pMIR reporter vector with NF1 3'UTR was stably transfected into HEK293 cells. Stably transfected cells were then transiently co-transfected with an empty vector (MDH1-PGK-GFP) or an miR-10b expression vector (MDH1-PGK-GFP/microRNA-10b, Addgene plasmid #16070) (Ma, et al. Nature 2007. 449:682-8) together with the pMIR-REPORT™ beta-galactosidase reporter control vector (Ambion, Austin, Tex.). Cells were collected 30 h after transfection, and the ratio of beta-galactosidase to firefly luciferase was measured with the Dual Luciferase Assay kit (Promega, Madison, Wis.).

miR-10b Over-Expression in HEK 293 Cells:

The MDH1-PGK-GFP/microRNA-10b (vector/miR-10b) or the MDH1-PGK-GFP vector (vector) was transfected into HEK 293T cells. The transfection rate was monitored by fluorescent microscopy. miR-10b expression level was confirmed by qRT-PCR. 48 h after transfection, cells were serum starved for 24 h and the protein and RNA were collected for Western blotting and qRT-PCR analyses.

Western Blotting:

Cells were cultured on 6-well or 12-well plates. After reaching 70-80% confluence, cells were serum-starved for 24 h in 0.2% FBS-containing medium to minimize the effects of growth factors presenting in the serum. Starved cells were lysed in RIPA buffer. Protein quantitation was determined by a BCA protein assay kit (Pierce, Rockford, Ill., USA). 20 μg of protein per lane were separated by SDS-polyacrylamide gel electrophoresis (SDS-PAGE). Separated proteins were transferred to a polyvinylidine difluoride membrane. The blotting membrane was incubated overnight at 4° C. with different primary antibodies: anti-p44/42 MAP Kinase (Cell Signaling, #9107, 1:1000), anti-phospho-p44/42 MAPK (Thr202/Tyr204) (Cell Signaling, #9106, 1:1000), anti-Phospho-S6 Ribosomal protein (ser235/236) (Cell Signaling, #4858, 1:1000), anti-neurofibromin (Santa Cruz, sc-67, 1:500) and anti-β-actin (Sigma, A5441, 1:1000). After washing with PBS three times, the blots were incubated for one hour at room temperature with a horseradish peroxidase-conjugated secondary antibody: anti-goat or mouse IgG (Chemicon, Temecula, Calif.), diluted 1:10,000. All signals were visualized using ECL plus chemiluminescence substrate (Amersham Pharmacia Biotech, Piscataway, N.J.).

Cell Proliferation:

MTT Assay:

ST8814 cells were plated on 96-well plates at a density of 1000 cells/well and allowed to attach to the plate overnight. Various miRNA inhibitors or precursors or controls were transfected into cells with Lipofectin (Invitrogen). After serum starvation for 24 h, the medium was replaced with 100 μl fresh medium containing 0.5 mg/ml MTT at indicated time points. After 4-hour incubation, the medium was removed and the purple blue sediment was dissolved in 150 μl of DMSO. The relative optical density (OD) for each well was determined using a WELLSCAN MK3 ELIASA (Labsystems, Dragon, Finland).

Colony Formation:

ST8814 cells transfected with an miR-10b inhibitor or a negative control were cultured on 6-well plate for 14 days. Transfected cells were washed with PBS for three times and fixed with 10% formalin for 20 minutes. After drying, cells were stained with 0.1% crystal violent solution for 30 minutes, washed with distilled water and dried. Colonies were counted by microscopy.

Cell Migration and Invasion:

ST8814 cells were transfected with various miRNA inhibitors, precursors, or controls. After 48-hour incubation, transfected cells were serum-starved for another 24 h and then pulsed with 5 μM of cell tracker green (Invitrogen) for 30 min. Labeled cells were trypsinized and replated in 0.2% FBS culture medium without growth factors at a density of 25,000 cells per well in a trans-well insert (3 μm pore size, BD Falcon) for the migration assay or 50,000 cells per well in matrigel-coated, growth-factor-reduced, invasion chambers (8 μm pore size, BD Biosciences) for the invasion assay. After 6-hour incubation for the migration assay or after 22-hour incubation for the invasion assay, cells were washed with PBS for three times and fixed with 4% paraformaldehyde for one hour. The cells on the apical side of each insert were scraped off, and those that had migrated to the basal side of the membrane were visualized under a Zeiss Axiovert 200M microscope at 10× magnification. Cell numbers were quantified in an automated fashion using Metamorph analysis software.

Figure 4:
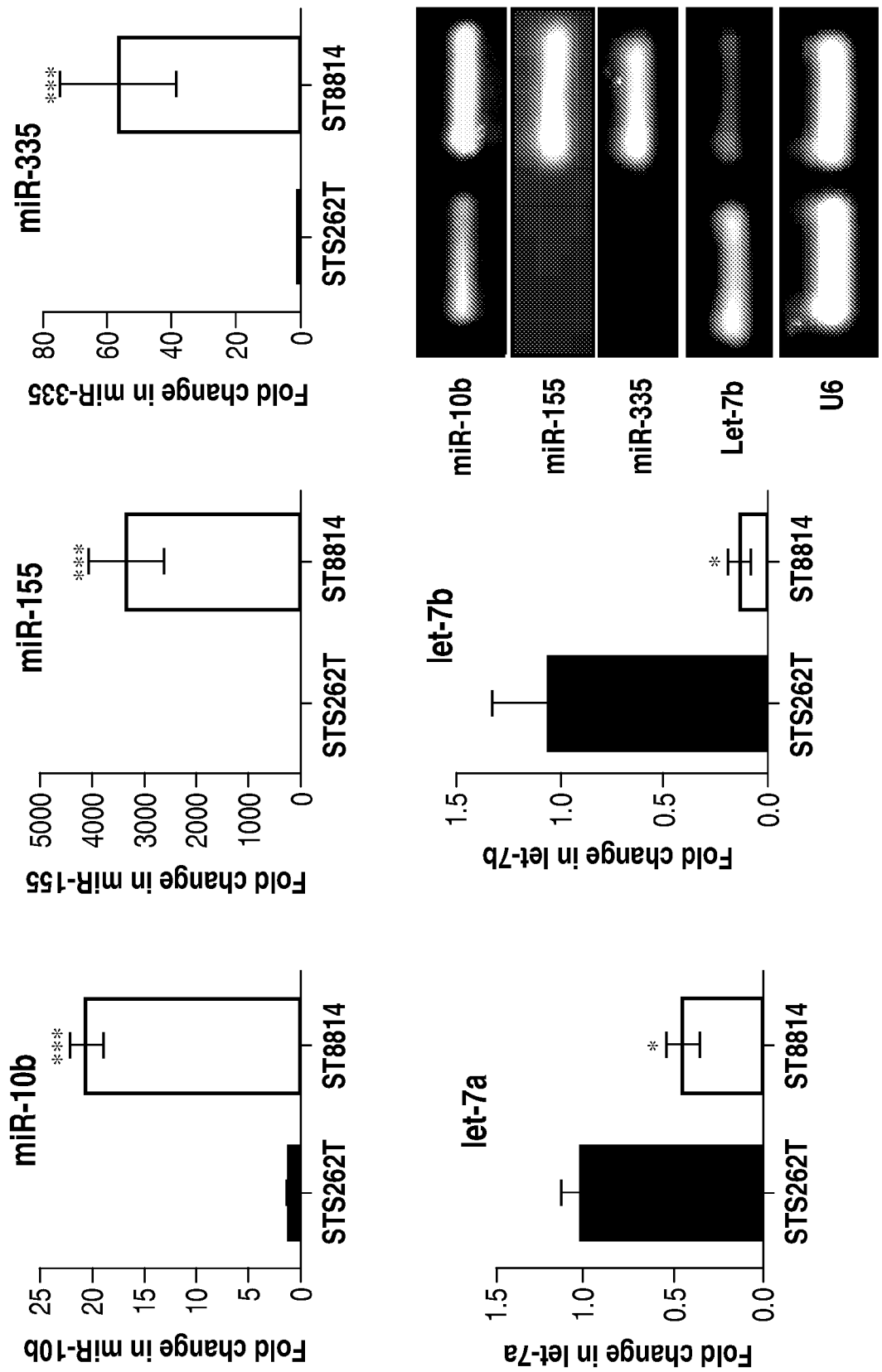
FIG. 4 depicts miRNA profiles in the NF1 MPNST cell line. miRNA expression in non-NF1 (ST262T) and NF1 (ST8814) associated MPNST cells was investigated by qRT-PCR. The expressions level of miR-10b, miR-155 and miR-335 were significantly higher in NF1 MPNST cells than in non-NF1 MPNST cells, while the expression levels of let-7a and let-7b were significantly lower in NF1 MPNST cells. The PCR products were electrophoresed in 5% agarose gels, and the result was consistent with the qRT-PCR data. ST8814 vs. ST262T: *$P<0.05$, ***$p<0.001$, n=3.
Figure 7B:
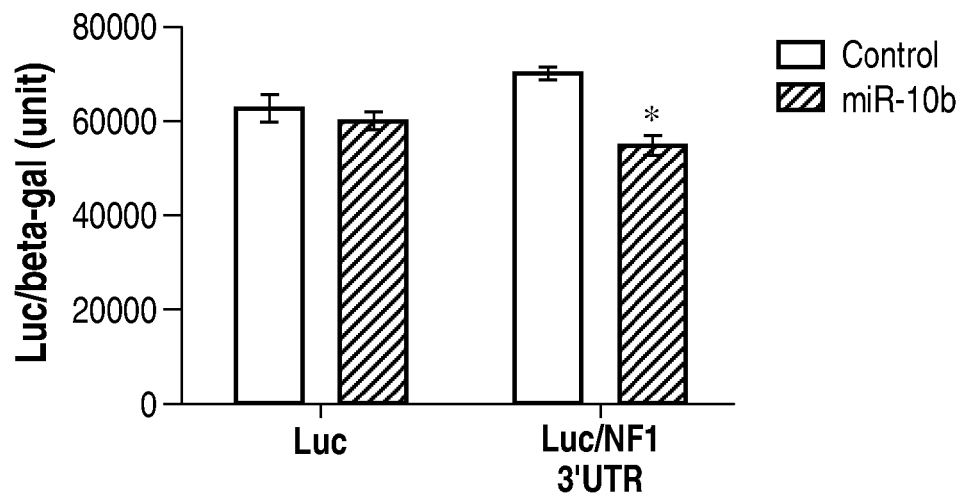
Figure 8A:
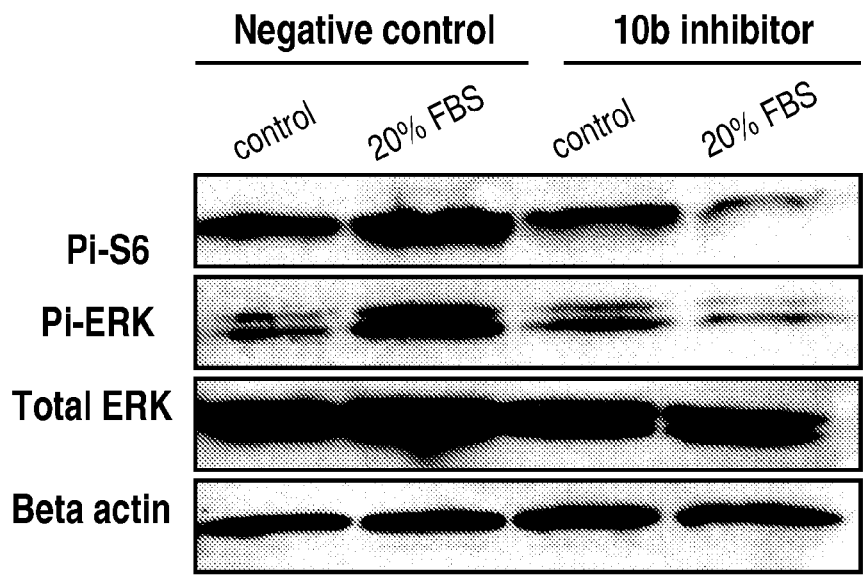
FIG. 8 provides results demonstrating that antisense inhibition of miR-10b corrected abnormal growth behaviors of NF1 MPNST cells. The miR-10b inhibitors or negative controls were transfected into NF1 MPNST cells (ST8814). A: The cells were serum-starved for 24 h, and then incubated in serum-free medium (control) or medium plus 20% FBS for 15 minutes. Phosphorylated ERK and S6 were detected by Western blotting. Compared to controls, inhibiting miR-10b expression reduced the phosphorylated ERK and S6 levels in response to serum stimulation. B: Inhibiting miR-10b expression significantly reduced cell proliferation at days 4-7 (n=5 each time point; MTT assay). C: Inhibiting miR-10b decreased colony formation. D: Inhibiting miR-10b significantly decreased cell migration and invasion (n=3). miR-10b inhibitor vs. negative control: *$P<0.05$, $P<0.01$, *$p<0.001$.
Figure 8B:
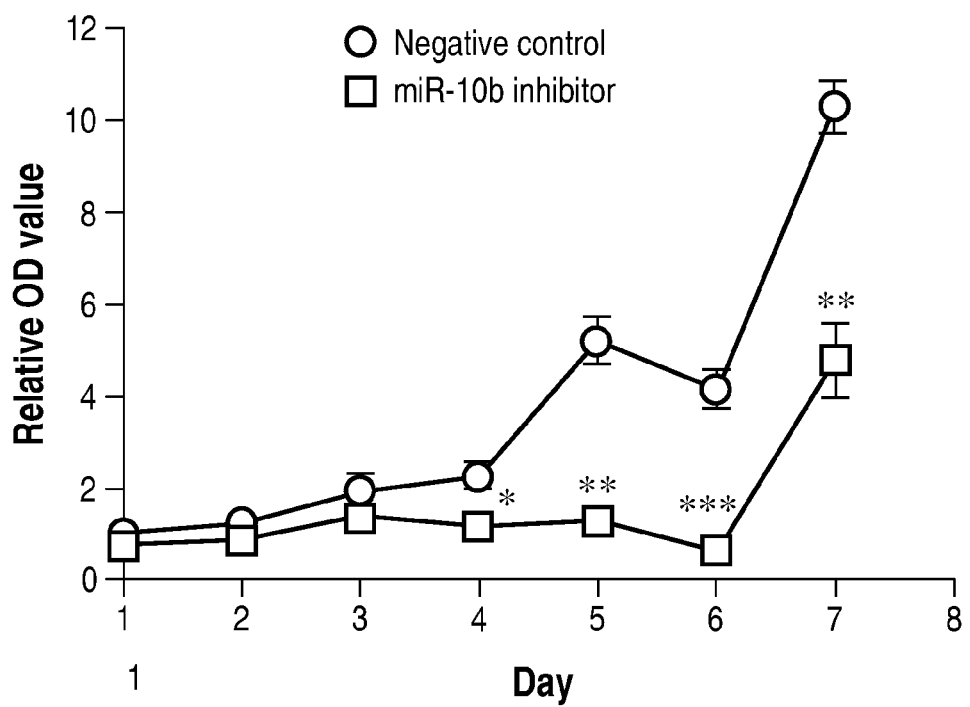
Figure 8C:
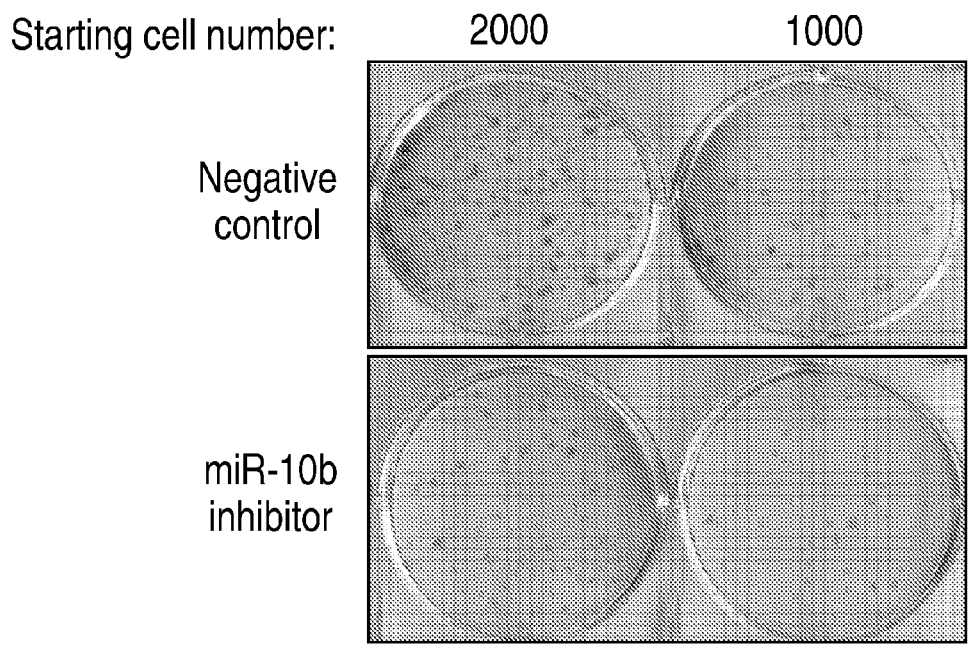
Figure 8D:
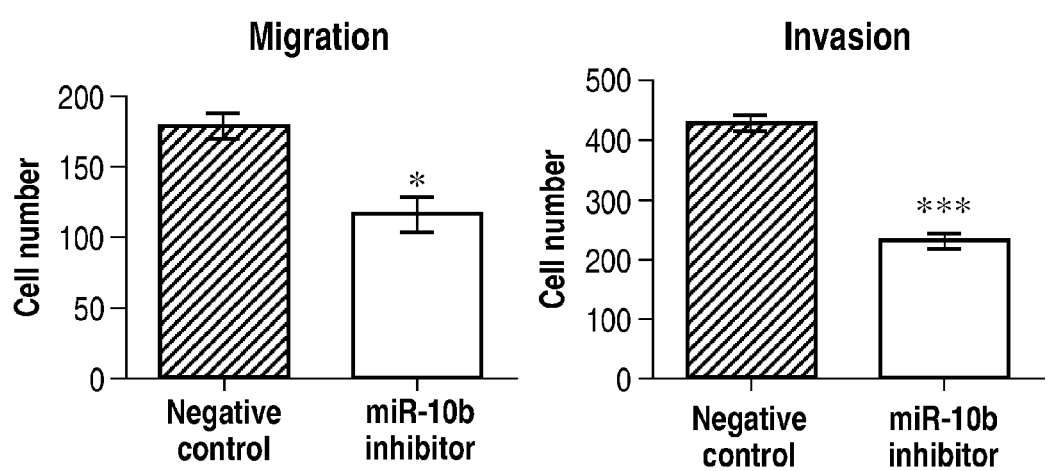
Figure 9A:
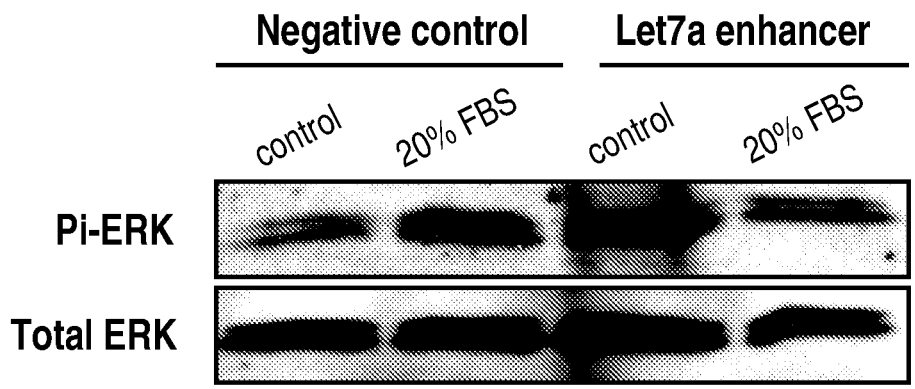
FIG. 9 shows the effects of restoring the expression of miR-155, miR-335 and let-7a in NF1 MPNST cells. The miR-155 inhibitors, miR-335 inhibitors, let-7a enhancers, or negative controls were transfected into NF1 MPNST cells (ST8814). A: enhancing let-7a expression reduced the phosphorylated ERK level in response to serum stimulation. B: Inhibiting miR-155 or miR335, or enhancing let-7a expression did not affect cell proliferation (n=5 each time point.
Figure 9B:
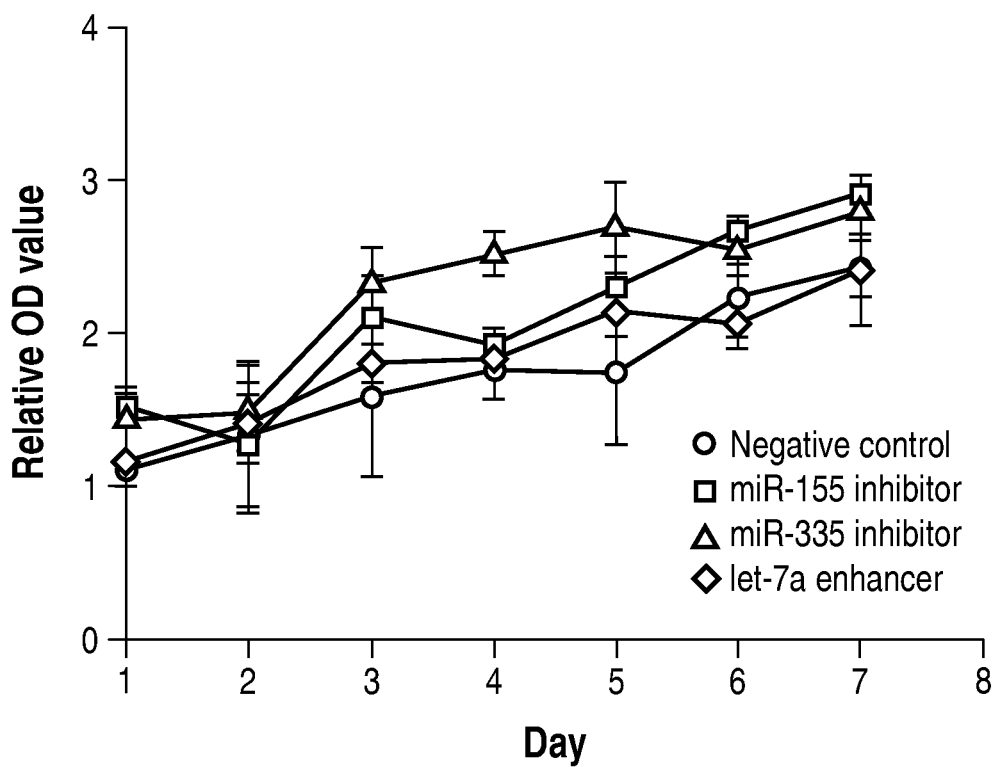
Figure 9C:
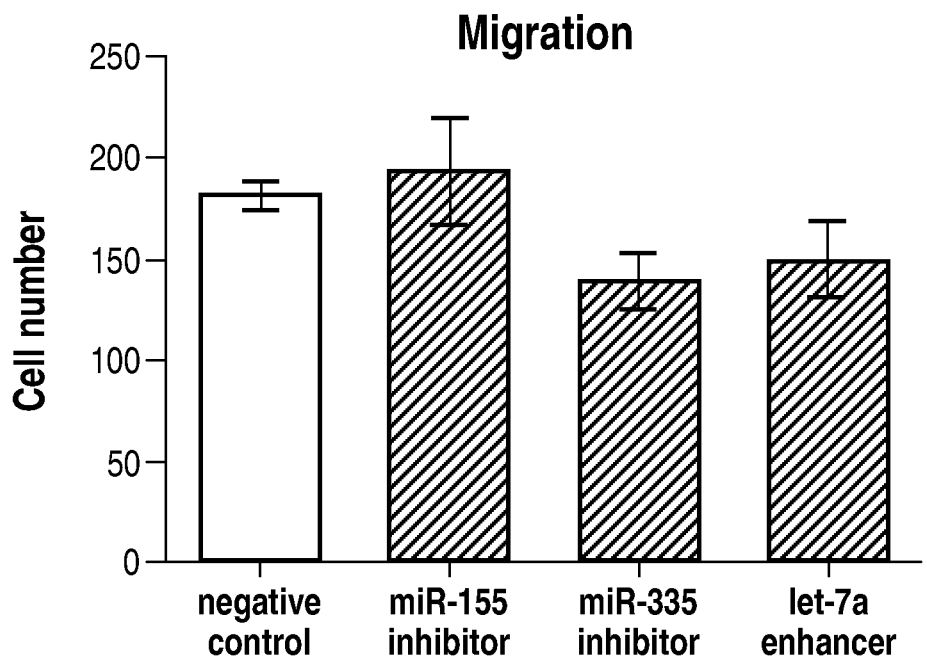

Statistical Analyses:

Analyses were performed with JMP 8.0 software (SAS Inc., Cary, N.C.). Unpaired t-tests were used to compare two groups, including two groups at different time points (FIG. 4 and FIG. 8B, D). ANOVA was used to compare multiple groups, followed by pairwise comparisons if significant differences were detected; Tukey-Kramer test for comparison of all groups (FIG. 5, 6), and Dunnett's test for comparison with a control group (FIGS. 9C and D). To determine the effects of both genetic manipulation (luciferase and luciferase/NF1 3'UTR) and treatments (control or miR-10b), a 2-way ANOVA and pairwise comparisons were used (FIG. 7B). Differences were considered statistically significant at P<0.05 on a two-tailed test. Data are expressed as means±standard error of the mean (SEM).

Example 2 miRNA Profiles in NF1 MPNST Cells miRNA profiles were first determined by microarray in ST8814 cells, a cell line derived from a human NF1 MPNST that does not express detectable neurofibromin (Fletcher, et al. N Engl J Med 1991. 324:436-42; Barkan, et al. Clin Cancer Res 2006. 12:5533-42), and in STS262T cells, a cell line derived from a sporadically occurring human non-NF1 MPNST that expresses a significant amount of neurofibromin (Barkan, et al. Clin Cancer Res 2006. 12:5533-42). In ST8814 cells, the expression levels of more than 70 miRNAs were significantly higher, while those of 40 miRNAs were significantly lower than in STS262T cells (see Table 2A and 2B below). The oncogenic miRNAs, miR-155, miR-10b and miR-335 (Ma, et al. Nature 2007. 449:682-8; Garzon, et al. Proc Natl Acad Sci USA 2008. 105:3945-50; E is, et al. Proc Natl Acad Sci USA 2005. 102:3627-32; Tavazoie, et al. Nature 2008. 451:147-52) were expressed at very high levels in ST8814 (density over 1800). Expression of the let-7 family members, let-7a, 7b, c, d, e, and f, which directly target RAS (Johnson, et al. Cell 2005. 120:635-47), was significantly lower in ST8814 than in STS262T cells.

TABLE 2A

Higher expression of miRNAs in ST8814 cell line

| Probe_ID | Sample A Signal (Non-NF1MPNST: STS262T) | Sample B Signal (NF1 MPNST: ST8814) | log2 (Sample B/ Sample A) |
|---|---|---|---|
| hsa-miR-155 | 57.52 | 15,133.97 | 8.07 |
| hsa-miR-10b | 40.17 | 2,344.19 | 6.03 |
| hsa-miR-335 | 52.42 | 1,852.52 | 5.21 |
| hsa-miR-323-3p | 4.87 | 120.28 | 5.11 |
| hsa-miR-337-3p | 6.19 | 174.83 | 4.77 |
| hsa-miR-34a | 12.42 | 208.50 | 4.08 |
| hsa-miR-335* | 46.33 | 577.63 | 3.66 |
| hsa-miR-9 | 48.39 | 563.35 | 3.56 |
| hsa-miR-433 | 17.52 | 166.52 | 3.56 |
| hsa-miR-495 | 67.99 | 676.81 | 3.32 |
| hsa-miR-148b | 12.91 | 125.93 | 3.28 |
| hsa-miR-9* | 14.30 | 116.50 | 3.25 |
| hsa-miR-199a-3p | 679.91 | 6,299.73 | 3.20 |
| hsa-miR-148a | 46.68 | 392.49 | 3.07 |
| hsa-miR-487b | 60.51 | 490.50 | 3.01 |
| hsa-miR-127-3p | 37.35 | 262.47 | 2.82 |
| hsa-miR-29c | 66.50 | 495.42 | 2.79 |
| hsa-miR-708 | 26.50 | 180.37 | 2.77 |
| hsa-miR-26b | 224.22 | 1,455.28 | 2.62 |
| hsa-miR-125b | 6,224.17 | 34,459.48 | 2.48 |
| hsa-miR-199a-5p | 76.14 | 379.47 | 2.48 |
| hsa-miR-432 | 168.12 | 925.78 | 2.44 |
| hsa-miR-21 | 12,670.62 | 67,784.34 | 2.42 |
| hsa-miR-494 | 73.66 | 413.70 | 2.39 |
| hsa-miR-454 | 144.83 | 740.69 | 2.36 |
| hsa-miR-431 | 29.19 | 147.87 | 2.32 |
| hsa-miR-130a | 123.39 | 611.45 | 2.31 |
| hsa-miR-376c | 36.58 | 185.54 | 2.30 |
| hsa-miR-301a | 35.45 | 161.54 | 2.27 |
| hsa-miR-376a | 26.89 | 129.43 | 2.24 |
| hsa-miR-29a | 2,296.57 | 10,274.54 | 2.18 |
| hsa-miR-379 | 80.60 | 332.51 | 2.13 |
| hsa-miR-411* | 31.61 | 136.78 | 2.13 |
| hsa-miR-342-3p | 101.68 | 434.09 | 2.10 |
| hsa-miR-382 | 91.83 | 385.59 | 2.07 |
| hsa-miR-218 | 103.61 | 456.61 | 2.04 |
| hsa-miR-143 | 152.98 | 612.40 | 2.01 |
| hsa-miR-26a | 2,343.89 | 9,243.94 | 1.96 |
| hsa-miR-224 | 281.34 | 1,047.83 | 1.95 |
| hsa-miR-20b | 185.83 | 718.35 | 1.92 |
| hsa-miR-10a | 123.84 | 420.24 | 1.87 |
| hsa-miR-151-3p | 234.50 | 789.68 | 1.75 |
| hsa-miR-126 | 48.25 | 152.58 | 1.66 |
| hsa-miR-181b | 313.66 | 893.79 | 1.62 |
| hsa-miR-151-5p | 2,330.69 | 6,713.89 | 1.54 |
| hsa-miR-195 | 77.39 | 214.45 | 1.47 |
| hsa-miR-28-5p | 223.27 | 606.70 | 1.46 |
| hsa-miR-214 | 1,357.21 | 3,712.12 | 1.45 |
| hsa-miR-152 | 142.07 | 372.37 | 1.34 |

TABLE 2A-continued

Higher expression of miRNAs in ST8814 cell line

| Probe_ID | Sample A Signal (Non-NF1MPNST: STS262T) | Sample B Signal (NF1 MPNST: ST8814) | log2 (Sample B/ Sample A) |
|---|---|---|---|
| hsa-miR-19b | 91.40 | 229.04 | 1.33 |
| hsa-miR-27b | 1,407.01 | 3,311.01 | 1.27 |
| hsa-miR-146b-5p | 136.44 | 312.16 | 1.19 |
| hsa-miR-27a | 1,264.30 | 2,725.89 | 1.19 |
| hsa-miR-30a | 184.96 | 357.14 | 0.95 |
| hsa-miR-17 | 858.03 | 1,639.27 | 0.94 |
| hsa-miR-20a | 1,196.22 | 2,273.57 | 0.93 |
| hsa-miR-106a | 839.57 | 1,596.06 | 0.92 |
| hsa-miR-99a | 490.52 | 944.60 | 0.85 |
| hsa-miR-128 | 400.72 | 691.24 | 0.79 |
| hsa-miR-181a | 488.32 | 758.90 | 0.64 |
| hsa-miR-92a | 7,089.58 | 10,631.99 | 0.58 |
| hsa-miR-15b | 6,864.93 | 9,985.57 | 0.58 |
| hsa-miR-106b | 639.26 | 941.63 | 0.56 |
| hsa-miR-92b | 3,401.76 | 4,969.81 | 0.54 |
| hsa-miR-125a-5p | 5,162.19 | 7,217.41 | 0.50 |
| hsa-miR-24 | 2,714.46 | 3,721.40 | 0.46 |
| hsa-miR-23b | 10,034.39 | 12,769.94 | 0.35 |
| hsa-miR-16 | 7,827.67 | 9,178.02 | 0.23 |
| hsa-miR-100 | 4,295.99 | 4,993.14 | 0.22 |
| hsa-miR-23a | 11,480.14 | 12,572.06 | 0.13 |

TABLE 2B

Lower expression of miRNAs in ST8814 cell line.

| Probe_ID | Sample A Signal (Non-NF1MPNST: STS262T) | Sample B Signal (NF1 MPNST: ST8814) | log2 (Sample B/ Sample A) |
|---|---|---|---|
| hsa-miR-200b | 279.99 | 1.00 | −7.99 |
| hsa-miR-1323 | 110.90 | 7.63 | −3.73 |
| hsa-miR-1290 | 294.86 | 23.73 | −3.55 |
| hsa-miR-98 | 2,174.17 | 210.09 | −3.42 |
| hsa-miR-1308 | 4,708.66 | 468.48 | −3.28 |
| hsa-miR-1275 | 2,550.47 | 281.91 | −3.24 |
| hsa-miR-374b | 378.84 | 47.97 | −2.98 |
| hsa-let-7b | 22,544.01 | 3,360.10 | −2.75 |
| hsa-miR-625* | 174.21 | 25.88 | −2.75 |
| hsa-miR-197 | 405.64 | 59.88 | −2.67 |
| hsa-miR-1246 | 33,407.81 | 6,686.78 | −2.32 |
| hsa-miR-431 | 29.19 | 147.87 | 2.32 |
| hsa-miR-503 | 249.57 | 51.62 | −2.31 |
| hsa-miR-1268 | 217.70 | 51.71 | −2.07 |
| hsa-miR-768-5p | 187.21 | 45.83 | −2.03 |
| hsa-miR-193a-5p | 649.89 | 183.46 | −1.86 |
| hsa-miR-361-5p | 2,066.10 | 737.97 | −1.48 |
| hsa-miR-191 | 1,975.56 | 716.38 | −1.47 |
| hsa-miR-145 | 1,777.21 | 689.32 | −1.38 |
| hsa-miR-1280 | 1,572.37 | 618.53 | −1.36 |
| hsa-miR-423-5p | 2,202.69 | 892.30 | −1.30 |
| hsa-let-7c | 27,521.95 | 11,369.75 | −1.27 |
| hsa-miR-548m | 799.17 | 334.93 | −1.25 |
| hsa-miR-877 | 464.44 | 211.58 | −1.18 |
| hsa-let-7f | 28,609.16 | 13,063.69 | −1.13 |
| hsa-miR-638 | 911.34 | 416.67 | −1.13 |
| hsa-miR-498 | 610.38 | 273.66 | −1.09 |
| hsa-miR-574-5p | 367.99 | 196.31 | −1.08 |
| hsa-miR-182 | 2,362.23 | 1,125.34 | −1.04 |
| hsa-let-7d | 25,880.96 | 12,514.49 | −1.04 |
| hsa-miR-455-3p | 401.23 | 211.33 | −1.01 |
| hsa-let-7e | 19,603.92 | 10,041.31 | −0.97 |
| hsa-miR-222 | 6,700.71 | 3,289.51 | −0.95 |
| hsa-let-7a | 33,107.49 | 18,875.83 | −0.79 |
| hsa-miR-221 | 3,664.27 | 2,093.86 | −0.77 |
| hsa-miR-196a | 759.94 | 469.59 | −0.69 |
| hsa-miR-1826 | 13,936.79 | 9,646.61 | −0.53 |

TABLE 2B-continued

Lower expression of miRNAs in ST8814 cell line.

| Probe_ID | Sample A Signal (Non-NF1MPNST: STS262T) | Sample B Signal (NF1 MPNST: ST8814) | log2 (Sample B/ Sample A) |
|---|---|---|---|
| hsa-miR-25 | 3,751.83 | 2,730.57 | −0.49 |
| hsa-let-7i | 5,511.24 | 4,257.94 | −0.38 |

Table 2A and 2B: miRNA profiles in NF1 MPNST cells.
Total RNA from ST8I4 and STS262T cells were labeled and hybridized on miRNA microarrays (LC Sciences, Houston, TX) (n=3). All differentially expressed miRNAs with p-value < 0.01 are listed. Signals represent median signal values of three repeated samples. Mature miRNAs are sorted separately according to differential ratios. The ratio values are presented in $\log_2$ scale for quick and easy assessing differential direction as well as magnitude. A positive $\log_2$ value indicates up regulation and a negative $\log_2$ value indicates down regulation.

Results from qRT-PCR were consistent with the microarray data. miR-155 was >3330 fold higher, miR-335 was ~56 fold higher, miR-10b was ~20 fold higher, let-7a was ~50% lower, and let-7b was ~90% lower in ST8814 cells than in ST262T cells (FIG. 4). All of these differences were statistically significant (P<0.05). For further analyses, we focused on the five miRNAs (miR-155, miR-10b, miR-335, let-7a and let-7b) whose expression levels showed the largest differences between the NF1 and non-NF1 MPNST cells.

Example 3 miRNA Profiles in Human NF1 Tumor Tissues

Figure 5:
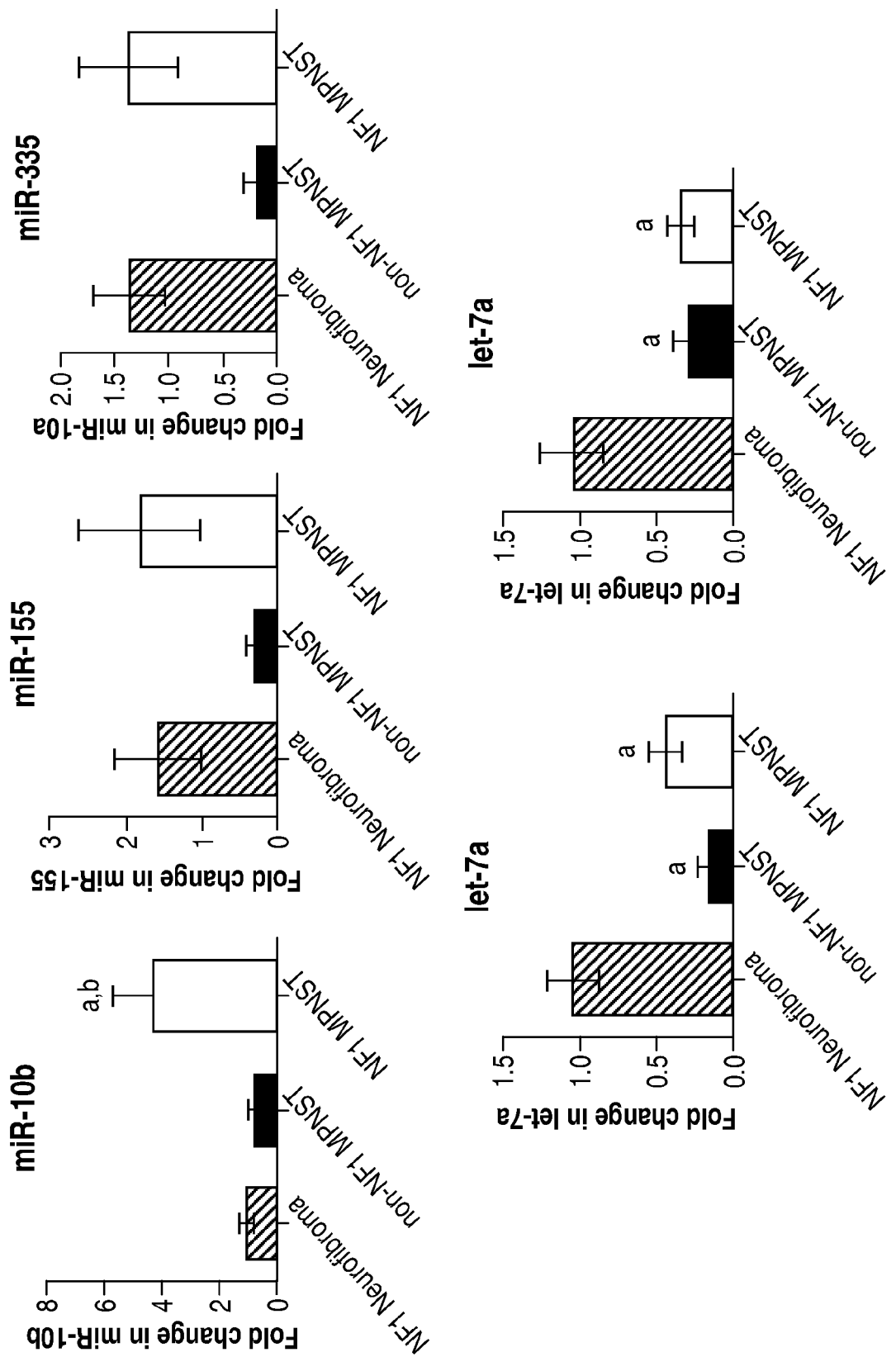
FIG. 5 depicts miRNA profiles in NF1 tumor tissues. Human NF1 tumor samples were divided into the NF1 neurofibroma group (n=13), the NF1 MPNST group (n=8) and the non-NF1 MPNST group (n=4) according to clinical and pathological diagnosis. miRNA expression was studied by qRT-PCR. Compared to the neurofibroma group, the expression level of miR-10b was significantly higher, while the expression levels of let-7a and let-7b were significantly lower in NF1 MPNST tissues. Compared to non-NF1 MPNST, the expression level of miR-10b was significantly higher in NF1 MPNST. There were no differences in the expression levels of miR-155 and miR-335 among the three groups. a: compared to NF1 neurofibromas, $P<0.05$; b: compared to non-NF1 MPNST, $P<0.05$.

To further investigate miRNA profiles in human NF1 tumor tissues, total RNA was isolated from frozen human NF1 MPNST tumor tissues (n=8, 6 males, 2 females, average age: 35) and non-NF1 MPNST tumor tissues (n=4, 2 males, 2 females, average age: 49), as well as benign NF1 neurofibroma tissues (n=13, 9 males, 4 females, average age: 37). Selected miRNA expression was determined by qRT-PCR. Neurofibromas are heterogeneous benign tumors composed of Schwann cells, fibroblasts, mast cells, and other cell types, and because most NF1 MPNST tumors are transformed from plexiform neurofibromas, benign neurofibromas were used for comparison. The expression of miR-10b was significantly higher only in NF1 MPNST tissues, while the expressions of let-7a and let-7b were significantly lower in both NF1 MPNST and non-NF1 MPNST tissues (FIG. 5). Compared to non-NF1 MPNST tissues, the expressions of miR-10b was significantly higher in NF1 MPNST tissues; the expressions of miR-155 and miR-335 appeared higher in NF1 MPNST tissues, however because of variability in the expression and limited sample size in non-NF1 MPNST tissues, the difference did not reach statistical significance (FIG. 5).

Example 4 miRNA Profiles in Primary Human NF1 Schwann Cells

Figure 6:
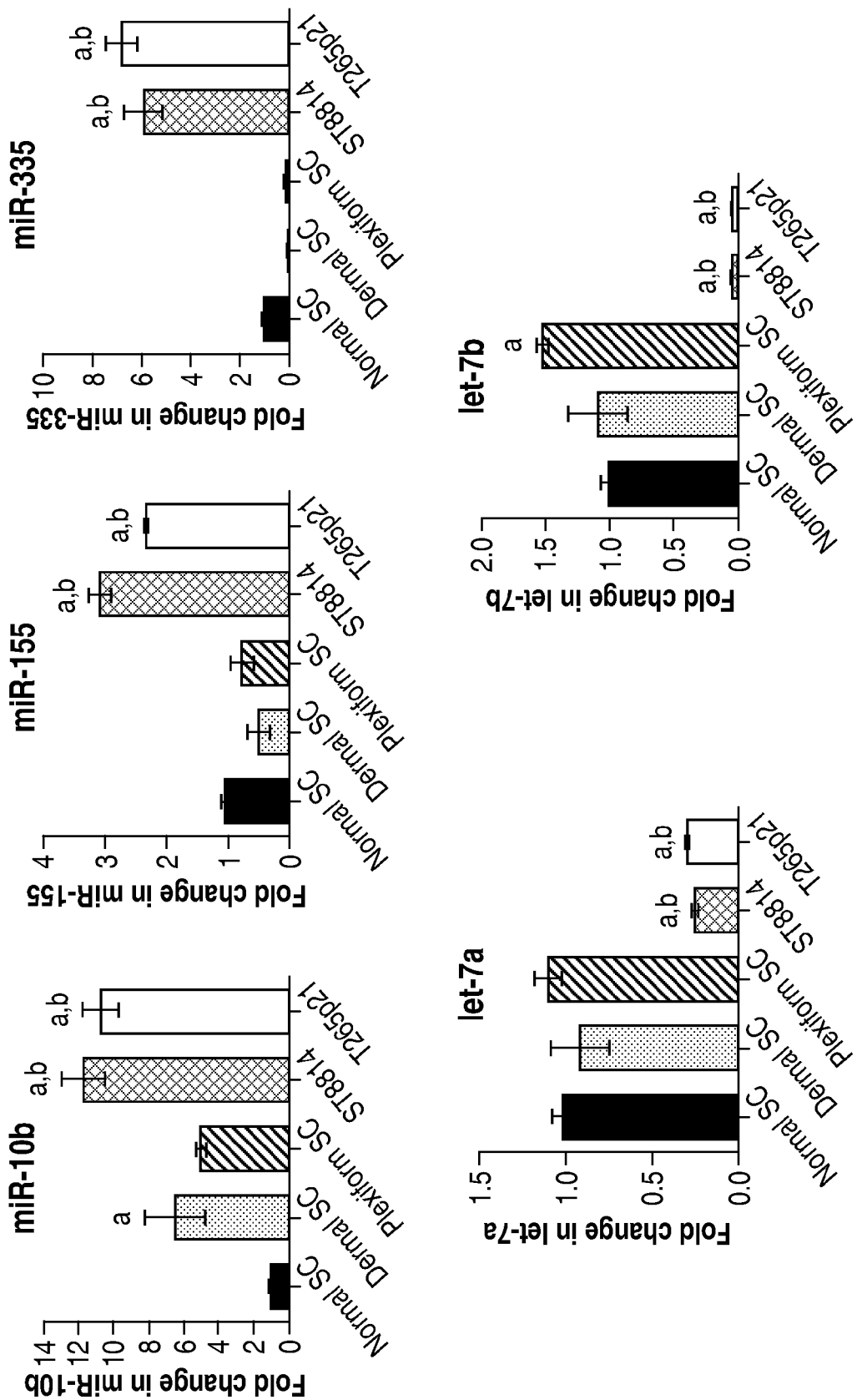
FIG. 6 depicts miRNA profiles in primary Schwann cells from NF1 neurofibromas. Primary Schwann cells were isolated from normal human adult sciatic nerves, and NF1 dermal and plexiform neurofibromas. NF1 MPNST cell lines ST8814 and T265p21 were also used for comparison. miRNA expression was studied by qRT-PCR. The miR-10b expression level was significantly higher in NF1 dermal Schwann cells than in normal Schwann cells, NF1 plexiform Schwann cells also showed higher miR-10b expression, but the difference was not statistically significant (P=0.07). The highest expression level of miR-10b was observed in NF1 MPNST cells. The expression levels of miR-155 and miR-335 were significantly higher in NF1 MPNST cells. The expression levels of let-7b and let-7a were significantly lower in NF1 MPNST cells. There were no significant differences in the expression levels of miR-155, miR-335, and let-7a between NF1 neurofibroma cells and normal Schwann cells. SC: Schwann cells. a: $P<0.05$ vs. normal SC; b: $P<0.05$ vs. dermal or plexiform SC; n=3-4.

Schwann cells are considered as the primary transformed cells in NF1 neurofibromas and MPNST. To further investigate miRNAs in NF1 tumorigenesis, primary Schwann cells were isolated from normal human adult sciatic nerves, NF1 dermal and plexiform neurofibromas, and used to compare with two NF1 MPNST cell lines, ST8814 and T265p21. miRNA expression was determined by qRT-PCR. miR-10b was the only miRNA whose expression was higher in primary Schwann cells from human NF1 dermal neurofibromas than in normal Schwann cells (FIG. 6, P<0.05). The miR-10b expression level appeared to be higher in NF1 plexiform Schwann cells, but the difference was not statistically significant (FIG. 6, P=0.07), perhaps due to small sample size. Of interest, the highest expression level of miR-10b was found in the NF1 MPNST ST8814 and T265p21 cells, with ~10-20 fold higher than that in normal Schwann cells (FIG. 6, P<0.05). Also the expression levels of miR-155 and miR-335 were significantly higher in NF1 MPNST cells than in normal Schwann cells, but not in Schwann cells from NF1 dermal or NF1 plexiform neurofibromas (FIG. 6, P<0.01). In contrast, the let-7a and let-7b expression levels were significantly lower in NF1 MPNST cells (FIG. 6, P<0.05). Collectively, our results indicate that NF1 MPNST cells had significantly higher expression levels of miR-10b, miR-155, miR-335 and significantly lower expression levels of let-7a and let-7b, compared to normal Schwann cells or NF1 Schwann cells from benign neurofibromas.

Figure 7A:
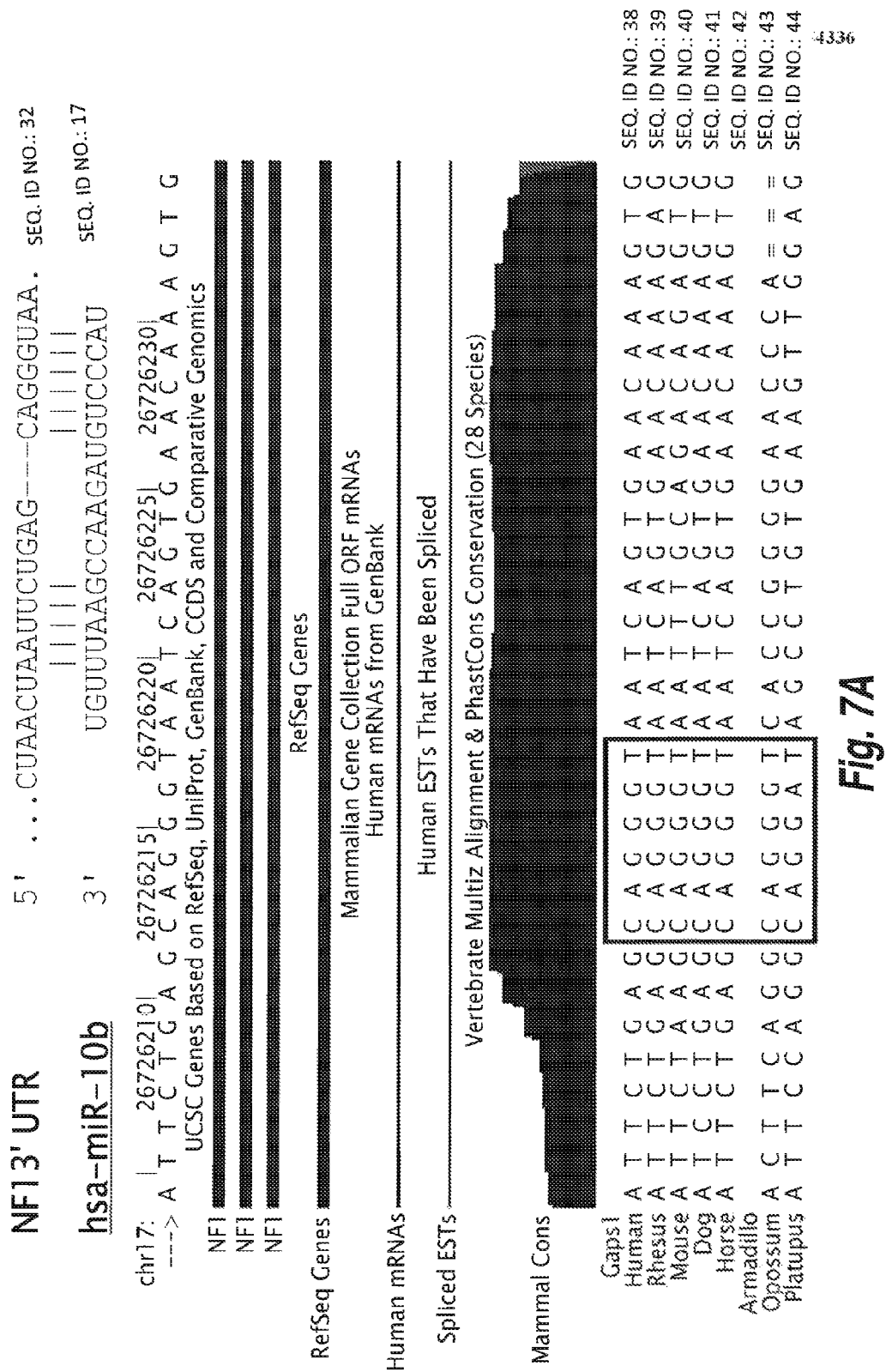
FIG. 7 shows that miR-10b directly targeted NF1 3'UTR. A: The 3'UTR of the NF1 gene was analyzed by TargetScan and a target sequence for miR-10b was identified. This target sequence was highly conserved across species. B: The NF1 3'UTR was cloned into the 3'UTR of the Luc reporter vector and the resulting construct was stably transfected into HEK293 cells. miR-10b cotransfection significantly reduced the expression of the Luc reporter containing the NF1 3'UTR, indicating that miR-10b directly targeted the NF1 3'UTR. C: The MDH1-PGK-GFP/microRNA-10b (vector/miR-10b) or MDH1-PGK-GFP vector (vector) was transfected into HEK293 cells. The transfection efficiency was monitored by fluorescence microscopy and the miR-10b expression level was confirmed by qRT-PCR. Over-expressing miR-10b suppressed neurofibromin expression. D: Transfected cells were stimulated with serum free medium (control) or medium supplemented with 20% fetal bovine serum (20% FBS) for 15 minutes, and the phosphorylated ERK and total ERK were analyzed by Western blotting. Over-expressing miR-10b induced higher phosphorylated ERK expression. *$P<0.05$ vs. control; n=3.

Example 5 miR-10b Directly Targets the 3' UTR of the NF1 mRNA and Suppresses Neurofibromin Expression An analysis using TargetScan (targetscan.org/) predicted that miRNA-10b, but not miR-155, miR-335 or let-7a/7b, could potentially target the 3' UTR of the NF1 mRNA (FIG. 7A). The seed sequence of the targeted site for miR-10b was highly conserved among NF1 mRNAs from various species (FIG. 7A), suggesting a regulating role for miR-10b in NF1 expression. To test this possibility, we cloned the NF1 3'UTR and placed it in the 3'UTR of a luciferase reporter gene. Co-transfection in HEK293 cells with either the miR-10b expression vector or a control vector showed that the luciferase activity was significantly reduced in cells co-transfected with miR-10b and the reporter construct containing the NF1 3'UTR, confirming that miR-10b directly targets 3'UTR of the NF1 mRNA (FIG. 7B, P<0.05).

Figure 7C:
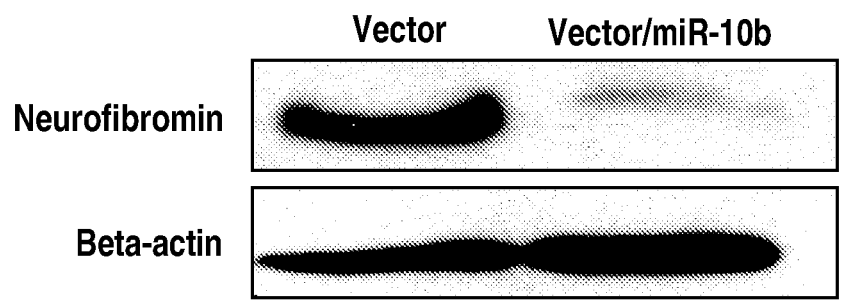
Figure 7D:
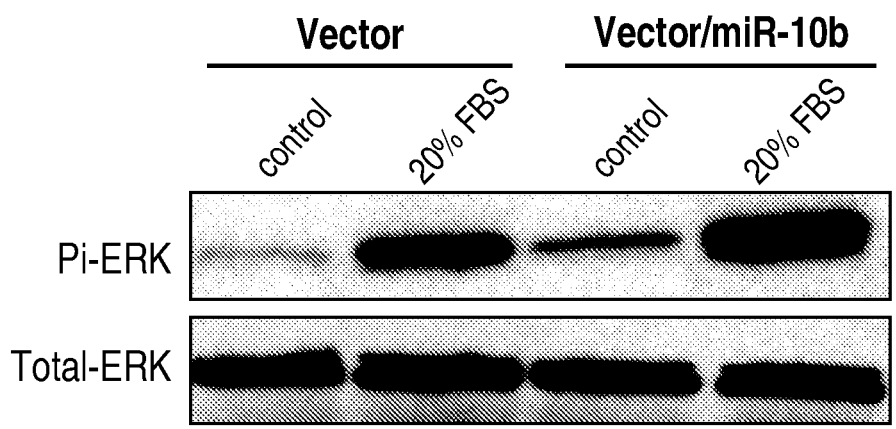

To further investigate the relationship between miR-10b and NF1, we over-expressed miR-10b in HEK293 cells. The mammalian expression vector MDH1-PGK-GFP/microRNA-10b and the control vector were tagged with a green fluorescent protein. We monitored the transfection efficiency by fluorescence microscopy. The miR-10b expression level was also confirmed by qRT-PCR (data not shown). HEK293 cells are NF1+/+ and expressed the neurofibromin protein when transfected with the control vector. Over-expression of miR-10b resulted in phenotypes similar to NF1-deficient cells with very a low level of neurofibromin and a high level of phosphorylated ERK levels, an index of RAS signaling (FIG. 7C, D). These results indicate that miRNA-10b directly targets the NF1 mRNA and suppresses neurofibromin expression.

Example 6

Antisense Inhibiting miR-10b Corrects the Abnormal Cellular Behaviors of NF1 MPNST Cells Because NF1 MPNST cells expressed high levels of miR-10b, we asked whether inhibiting miR-10b could revert the abnormally cellular behaviors of NF1 MPNST cells. ST8814 cells were transfected with an miR-10b antisense inhibitor or with a negative control (a similar antisense sequence as the miR-10b antisense inhibitor but does not inhibit known miR-NAs). Western blotting was used to assess the levels of phosphorylated ERK and S6, indicators for the MAPK and mTOR signaling pathways, respectively (both are the downstream RAS signals). Compared to control, ST8814 cells transfected with the miR-10b inhibitor had lower levels of phosphorylated ERK and S6 after serum stimulation (FIG. 8A). Concomitantly, inhibiting miR-10b resulted in significantly decreased cell proliferation, migration and invasion (FIG. 8B, C, D). In contrast, inhibiting miR-10b in non-NF1 MPNST cells (STS262T) had no effects on their growth characteristics (data not shown). Together, these results suggest that mi-10b plays an important role in NF1 MPNST progression.

Example 7

Effects of Restoring mi-155, mi-335 and let-7a and let-7b in NF1 MPNST Cells

Figure 9D:
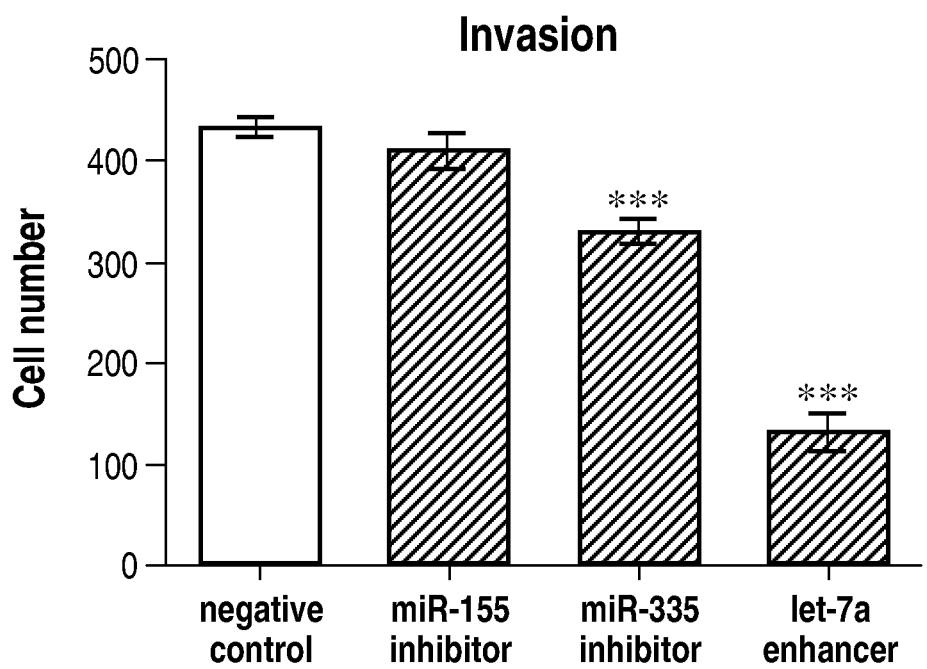

To determine whether upregulation of miR-155 and miR-335 and downregulation of let-7 family have any roles in any NF1 MPNST growth properties, we targeted restoring these miRNA functions using the antisense inhibitors for miR-155 and miR-335, or an enhancer for let-7a in ST8814 cells. Compared to control, ST8814 cells transfected with the let-7a enhancer had lower level of phosphorylated ERK after serum stimulation (FIG. 9A), while the antisense inhibitors for miR-155 and miR-335 did not affect the level of phosphorylated ERK (data not shown). Although restoring these miRNAs did not alter proliferation or migration of the ST8814 cells (FIG. 9B, C), inhibiting miR-335 or enhancing let-7a resulted in a significant reduction of cell invasion (FIG. 9D). These results suggest that miR-335 and let-7 may have roles in the progression of MPNST.

EQUIVALENTS

Those skilled in the art will recognize, or be able to ascertain using no more than routine experimentation, many equivalents to the specific embodiments of the invention described herein. Such equivalents are intended to be encompassed by the following claims.

---

The invention claimed is:

1. A method of increasing neurofibromin expression in a neural cell of a subject having neurofibromatosis type 1 comprising contacting the cell with an effective amount of a miR-10b inhibitor which downmodulates the level of miR-10 miRNA in the neural cell, such that neurofibromin expression in the neural cell is increased.

2. The method of claim 1, wherein the miR-10b inhibitor is an miR-10b antigomir comprising a nucleotide sequence having complementarity to miR-10b.

3. The method of claim 2, wherein the miR-10b antigomir comprises the nucleotide sequence 5'-CACAAATTCGGT-TCTACAGGGTA-3' [SEQ. ID NO.1].

4. The method of claim 2, wherein the antigomir comprises at least one stabilizing modification.

5. The method of claim 4, wherein the at least one stabilizing modification comprises a phosphorothioate backbone.

6. The method of claim 4, wherein the at least one stabilizing modification comprises at least one nucleotide having a 2'-sugar modification.

7. The method of claim 1, wherein the miR-10b inhibitor inhibits miR-10b indirectly by inhibiting TWIST1.

8. The method of claim 2, wherein the antigomir is 19 to 24 nucleotides in length.

9. The method of claim 2, wherein the antigomir has at least 95% percent complementarity to the miRNA over its full length, and wherein the 8 nucleotides at the 5' end of the antigomir are 100% complementary to the corresponding nucleotides of the miRNA.

10. The method of claim 2, wherein the antigomir comprises a cholesterol modification.

* * * * *